(12) United States Patent
Murphy et al.

(10) Patent No.: US 10,765,084 B2
(45) Date of Patent: Sep. 8, 2020

(54) METHOD FOR IMPROVING THE MEAN DRY SHOOT WEIGHT, MEAN DRY GRAIN WEIGHT, AND SUPPRESSING SEED-BORNE INFECTION IN A CEREAL CROP

(71) Applicants: The Provost, Fellows, Scholars and other members of Board of Trinity College Dublin, Dublin (IE); University College Dublin, National University of Ireland, Dublin, Dublin (IE)

(72) Inventors: Brian Murphy, County Dublin (IE); Trevor Hodkinson, Dublin (IE); Fiona Doohan, County Donegal (IE)

(73) Assignees: The Provost, Fellows, Foundation Scholars & the Other Members of Board, of the College of the Holy & Undivided Trinity of Queen Elizabeth, Near Dublin, Dublin (IE); University College Dublin, National University of Ireland, Dublin, Dublin (IE)

( * ) Notice: Subject to any disclaimer, the term of this patent is extended or adjusted under 35 U.S.C. 154(b) by 446 days.

(21) Appl. No.: 15/507,585

(22) PCT Filed: Aug. 29, 2015

(86) PCT No.: PCT/EP2015/069809
§ 371 (c)(1),
(2) Date: Feb. 28, 2017

(87) PCT Pub. No.: WO2016/030535
PCT Pub. Date: Mar. 3, 2016

(65) Prior Publication Data
US 2017/0273271 A1 Sep. 28, 2017

(30) Foreign Application Priority Data
Aug. 29, 2014 (EP) .................................... 14182893

(51) Int. Cl.
*A01H 17/00* (2006.01)
*A01C 1/06* (2006.01)
*A01N 63/30* (2020.01)
*A01C 1/08* (2006.01)

(52) U.S. Cl.
CPC .............. *A01H 17/00* (2013.01); *A01C 1/06* (2013.01); *A01C 1/08* (2013.01); *A01N 63/30* (2020.01)

(58) Field of Classification Search
CPC ...................................................... A01H 17/00
See application file for complete search history.

(56) References Cited

U.S. PATENT DOCUMENTS

2003/0195117 A1   10/2003   Imada et al.
2012/0144533 A1*   6/2012   Craven .................. A01N 63/04
                                                        800/300

FOREIGN PATENT DOCUMENTS

GB            2490249 A      10/2012
WO    WO-2014/121366 A1       8/2014

OTHER PUBLICATIONS

Murphy et al BioControl vol. 60 pp. 281-292 (Year: 2015).*
Achatz et al "Root Colonization by Piriformospora Indica Enhances Grain Yield in Barley Under Diverse Nutrient Regimes by Accelerating Plant Development" Plant Soil vol. 333, pp. 59-70, 2010.
Murphy "Fungal Infection in Barley Roots—Friend and Foe" Endophytes for Plant Protection: The State of the Art, pp. 102-116, 2013.
Murphy et al "Yield Increase Induced by the Fungal Root Endophyte Piriformospora Indica in Barley Grown at Low Temperature is Nutrient Limited" Symbiosis vol. 62, pp. 29-39, 2014.
Nilsson et al "Intraspecific ITS Variability in the Kingdom Fungi as Expressed in the International Sequence Databases and its Implications for Molecular Species Identification" Evolutionary Bioinformatics vol. 4, pp. 193-201, 2008.
Porras-Alfaro et al "Hidden Fungi, Emergent Properties: Endophytes and Microbiomes" Annual Review of Phytopathology vol. 49, pp. 291-315, 2011.

\* cited by examiner

*Primary Examiner* — David H Kruse
(74) *Attorney, Agent, or Firm* — Cesari and McKenna, LLP

(57) ABSTRACT

A seed coating composition comprising a mixture of a fungal root endophyte isolated from a root of the plant found in low-nutrient, drought-stressed or multiply-stressed conditions and a carrier medium for application of said composition to a target seed, wherein the endophyte is characterised in having a nuclear ribosomal internal transcribed spacer (nr ITS) with at least a 90% sequence identity to any one of SEQ ID NOs: 3 to 15.

20 Claims, 3 Drawing Sheets
Specification includes a Sequence Listing.

SEQUENCE LISTING

<160> NUMBER OF SEQ ID NOS: 15

<210> SEQ ID NO 1
<211> LENGTH: 19
<212> TYPE: DNA
<213> ORGANISM: Artificial Sequence
<220> FEATURE:
<223> OTHER INFORMATION: Forward Primer

<400> SEQUENCE: 1
tccgtaggtg aacctgcgg                                                  19

<210> SEQ ID NO 2
<211> LENGTH: 20
<212> TYPE: DNA
<213> ORGANISM: Artificial Sequence
<220> FEATURE:
<223> OTHER INFORMATION: Reverse Primer

<400> SEQUENCE: 2
tcctccgctt attgatatgc                                                 20

<210> SEQ ID NO 3
<211> LENGTH: 541
<212> TYPE: DNA
<213> ORGANISM: Unknown
<220> FEATURE:
<223> OTHER INFORMATION: nuclear ribosomal internal transcribed spacer
      (nrITS) sequence

<400> SEQUENCE: 3
ctcccaaaac ccactgtgac atataccttt gttttcgttg cctcggcggg gtcgtgctcc      60
ctggaaacag gggttcgcgc cgccgggtga cacctaaacc ctgatttaat tacagaagtc     120
tttctgagta aaacattcta aatgaatcaa aactttcaac aacggatctc ttggttctgg     180
catcgatgaa gaacgcagcg aaatgcgata agtaatgtga attgcagaat tcagtgaatc     240
atcgaatctt tgaacgcaca ttgcgcccgc cagtattctg gcgggcatgc ctgttcgagc     300
gtcatttcaa ccctcaagac cccttcgggg gacttggtgt tggggaccgg ctgttcccgg     360
cctgcttctt gcagcgcctt tatgccgccc ccgaaatgaa ttggcggcct cgtcgcggcc     420
tcccctgcgt agtagcacaa cctcgcaacg ggaacgtgac ggcggccctg ccgtaaacaa     480
cccaatttta ttaaagttga cctcgaatca gggaggatac ccgctgaact taagcatatc     540
a                                                                    541

<210> SEQ ID NO 4
<211> LENGTH: 335
<212> TYPE: DNA
<213> ORGANISM: Unknown
<220> FEATURE:
<223> OTHER INFORMATION: nuclear ribosomal internal transcribed spacer
      (nrITS) sequence

<400> SEQUENCE: 4

```
aaaccattac aacctgcaac gatggatctc ttggctctgg catcgatgaa gaacgcagcg    60
aaatgcgata cgtaatgtga attgcagatc tctcagtgaa tcatcgagtt tttgaacgca   120
catagcgccc gccagcattc tggcgggcat ggcctgtccg agcgtcgatg acgcctgctc   180
gagcgctgcc gctcggtgtt ggggcgctag gggcctcgcc ccctaggccc tctaagaaga   240
agtgcgcggt ccacgacggg ccccgggtac agtaatttat tgctgcccta gggagccgcc   300
gggcgggctt ggccgtaaaa cccccgacat aggcc                              335
```

<210> SEQ ID NO 5
<211> LENGTH: 502
<212> TYPE: DNA
<213> ORGANISM: Unknown
<220> FEATURE:
<223> OTHER INFORMATION: nuclear ribosomal internal transcribed spacer
      (nrITS) sequence

<400> SEQUENCE: 5

```
cgggatgttc ataacccttt gttgtccgac tctgttgcct ccggggcgac cctgccttcg    60 ggcggggct ccgggtggac acttcaaact cttgcgtaac tttgcagtct gagtaaactt   120
aattaataaa ttaaaacttt taacaacgga tctcttggtt ctggcatcga tgaagaacgc   180
agcgaaatgc gataagtaat gtgaattgca gaattcagtg aatcatcgaa tctttgaacg   240
cacattgcgc ccctggtat tccgggggc atgcctgttc gagcgtcatt tcaccactca    300
agcctcgctt ggtattgggc aacgcggtcc gccgcgtgcc tcaaatcgtc cggctgggtc   360
ttctgtccct aagcgttgtg gaaactattc gctaaagggt gttcgggagg ctacgccgta   420
aaaacaaccc catttctaag gttgacctcg gatcaggtag ggatacccgc tgaacttaag   480
catatcataa cgcgggagaa aa                                            502
```

<210> SEQ ID NO 6
<211> LENGTH: 332
<212> TYPE: DNA
<213> ORGANISM: Unknown
<220> FEATURE:
<223> OTHER INFORMATION: nuclear ribosomal internal transcribed spacer
      (nrITS) sequence

<400> SEQUENCE: 6

```
gatatctgtc cgcgtctccg cgctcgccga agacaccttaa gaactctgtc tgaagattgt    60
agtctgagat taaatataaa ttatttaaaa ctttcaacaa cggatctctt ggttccggca   120
tcgatgaaga acgcaccgaa atgcgatacg taatgtgaat tgcagaattc agtgaatcat   180
cgagtctttg aacgcacatt gcgccctctg gtattccgga gggcatgctg tccgagcgtc   240
attgctgcct caagcacggt tgtgtgtggg ctccgtcctc cttccgggga cgggcccgaa   300
ggcgcgcggc cccgccggcc tcagcgatgg gg                                 332
```

<210> SEQ ID NO 7
<211> LENGTH: 479
<212> TYPE: DNA
<213> ORGANISM: Unknown
<220> FEATURE:
<223> OTHER INFORMATION: nuclear ribosomal internal transcribed spacer
      (nrITS) sequence

<400> SEQUENCE: 7

```
cctgtctgac ccttgtcttt tgcgtactat ttgtttcctc ggtgggcttg cctgccgata    60
```

```
ggacaaccat taaacctttt gtaattgcaa tcagcgtcag aaaaaacata atagttacaa      120
ctttcaacaa cggatctctt ggttctggca tcgatgaaga acgcagcgaa atgcgaaaag      180
tagtgtgaat tgcagaattc agtgaatcat cgaatctttg aacgcacatt gcgccccttg      240
gtattccatg gggcatgcct gttcgagcgt catttgtacc ttcaagccct gcttggtgtt      300
gggtgtttgt cccgctttgt gcgtggactc gcctcaaagc aattggcagc cggcgtacta      360
gcctgggagc gcagcacatt tgcgcatct tgtcttgaac gcttgcgtcc atgaagccta       420
cattttaact cttgacctcg gatcaggtag ggatacccgc tgaacttaag catatcaaa      479
```

<210> SEQ ID NO 8
<211> LENGTH: 541
<212> TYPE: DNA
<213> ORGANISM: Unknown
<220> FEATURE:
<223> OTHER INFORMATION: nuclear ribosomal internal transcribed spacer
      (nrITS) sequence

<400> SEQUENCE: 8

```
ccaaccctg tgattatacc tttaattgtt gcttcggcgg gacttcgcgc ccgccgggga       60
cccaaacctt ctgaattttt taataagtat cttctgagtg gttaaaaaaa tgaatcaaaa      120
ctttcaacaa cggatctctt ggttctggca tcgatgaaga acgcagcgaa atgcgataag      180
taatgtgaat tgcagaattc agtgaatcat cgaatctttg aacgcacatt gcgcccgtca      240
gtattctggc gggcatgcct gttcgagcgt cattacgccc ctcaagtccc ctgtgggact      300
tggtgttggg gatcggcgag gcttggtttt ccagcgcagc cgtccctcaa atcaattggc      360
gggtctcgcc cgtggccctc cctctgcgca gtagtaaaaa ccacctccgc aacaggagcc      420
cggcgccgtt cccactgccc gtaaaaaccc cccaacttt tttatagttg acctccggaa       480
tcagggtaag gactaccccg cctgaaactt aaagcatatc taaagcgggg ggagagagaa      540
a                                                                      541
```

<210> SEQ ID NO 9
<211> LENGTH: 517
<212> TYPE: DNA
<213> ORGANISM: Unknown
<220> FEATURE:
<223> OTHER INFORMATION: nuclear ribosomal internal transcribed spacer
      (nrITS) sequence

<400> SEQUENCE: 9

```
ccctcactat ttcttatttg cagagtatgc cgcggtcagg cttcccctgc caggagtgag      60
tctggcagca catcctcatt gcaactacga gagcggtccc gcctacggca gctacttatc      120
gacacgagct gttgactagt gcctactaat gttcctcgtt gaagggcaat aattgctatg      180
ctcgttggcc aaaacgccga ggtgccataa aattggcaga actcttggga ttcagaggga      240
ctttgaccgg taatggcttt ccccaggttc ccctaccaaa aacttctctg agccttcgtg      300
atgtccacaa gctacgttgg tgagtagggt tccgccttct ctcctggggg aagggcaaga      360
aaggcagcgg cggtaccgcg tccggtcctc aagcgtatgg ggctttgtca cccgctttgt      420
aggatggccg gcgccgccga tcaaccaaac tttttccagg ttgacctcgg atcaggtagg      480
gttacccgct gaacttagca tatcataagc ggagaaa                              517
```

<210> SEQ ID NO 10
<211> LENGTH: 419
<212> TYPE: DNA

<213> ORGANISM: Unknown
<220> FEATURE:
<223> OTHER INFORMATION: nuclear ribosomal internal transcribed spacer
      (nrITS) sequence

<400> SEQUENCE: 10

```
atgtctttgt ctgagtgttc tcttttaaat ccagctaatc tttcaacaac ggatctcttg    60
gttctggcat cgatgaagaa cgcagcgaaa tgcgataagt aatgcgaatt gcagaattct   120
cgtgagtcat cgaatctttg aacgcacatt gcgccctttg gtattccgaa gggcatgcct   180
gttcgagcgt cattttcacc cctcaagccc ccggcttggt gttggacggt ctggtccggg   240
gacctcaaac cccctggacc cctcccaaag acaatgacgg cgggctgttg aaccccggt    300 acactggagc atcttcacgg agcacgtacc ggtctcaagg gtcgacggca cccggtctat   360
acctatattt ttcaaggttg acctcggatc aggtaggaat acccgctgaa cttaagcat    419
```

<210> SEQ ID NO 11
<211> LENGTH: 575
<212> TYPE: DNA
<213> ORGANISM: Unknown
<220> FEATURE:
<223> OTHER INFORMATION: nuclear ribosomal internal transcribed spacer
      (nrITS) sequence

<400> SEQUENCE: 11

```
cgtgttttat tttaccttgt tgcttcggcg agcctgcctt ttggctgccg ggggacatct    60
gtccccgggt ccgcgctcgc cgaagacacc ttagaactct gtctgaagat tgtagtctga   120
gattaaatat aaattattta aaactttcaa caacggatct cttggttccg gcatcgatga   180
agaacgcagc gaaatgcgat acgtaatgtg aattgcagaa ttcagtgaat catcgagtct   240
ttgaacgcac attgcgccct ctggtattcc ggagggcatg cctgtccgag cgtcattgct   300
gccctcaagc acggcttgtg tgttgggctc cgtcctcctt ccggggacg ggcccgaaag    360 gcagcggcgg caccgcgtcc ggtcctcaag cgtatgggc tttgtcaccc cgctttgtag    420
gactggccgg cgcctgccga tcaaccaaac tttttttccag gttgacctcg gatcaggtag   480 gggataccccg ctgaacttaa gcatatcata ggcgggagga aaggagctac ggggattgcc   540
ccagtaacgg cgagtgaagc gcaagagctc agatt                              575
```

<210> SEQ ID NO 12
<211> LENGTH: 598
<212> TYPE: DNA
<213> ORGANISM: Unknown
<220> FEATURE:
<223> OTHER INFORMATION: nuclear ribosomal internal transcribed spacer
      (nrITS) sequence

<400> SEQUENCE: 12

```
gtttatttta accttgttgc ttcggcgagc cttgcctttt ggctgccggg ggacatctgt    60
ccccgggtcc gcgctcgccg aagacacctt agaactctgt ctgaagattg tagtctgaga   120
ttaaatataa attatttaaa actttcaaca acggatctct tggttccggc atcgatgaag   180
aacgcagcga aatgcgatac gtaatgtgaa ttgcagaatt cagtgaatca tcgagtcttt   240
gaacgcacat tgcgccctct ggtattccgg agggcatgcc tgtccgagcg tcattgctgc   300
cctcaagcac ggcttgtgtg ttgggctccg tcctccttcc ggggacggg cccgaaaggc    360 agcggcggca ccgcgtccgg tcctcaagcg tatgggctt tgtcacccccg ctttgtagga   420 ctggccggcg cctgccgatc aaccaaactt ttttccaggt tgacctcgga tcaggtaggg   480
```

```
ataccegetg aacttaagca tatcataagc gcggaaggga aacagaacct acgggagatt        540 gecccataac agcgagtgaa gcgcaagagc tcaatttgta agtcggctcc tcgggtcc         598
```

```
<210> SEQ ID NO 13
<211> LENGTH: 550
<212> TYPE: DNA
<213> ORGANISM: Unknown
<220> FEATURE:
<223> OTHER INFORMATION: nuclear ribosomal internal transcribed spacer
      (nrITS) sequence

<400> SEQUENCE: 13
accggcgtag cctcccgaac acccttagc gaatagtttc cacaacgctt aggggacaga        60
agtacccagc cggacgaatt ttgaaggcac gcggcggaac cgcgtttgcc caataccaag      120
cgaggctttg agtgggtgaa aatgaacgcc ttcgaaacag ggcatggccc ccccgggaa       180 ataaccaggg ggggccgcca atggtgccgt ttcaaaggaa tttcgattga atttcactgg     240
aaatttctgg caaatttcac atttaactta ttcgcatttt tcgctgccgt ttctttcatt    300
cgattgccca gaaaccaaag aggaatccgt tggttaaaag gttttaattt taattaaatt    360
aaagtttaac ttcagaactg caaaggttaa cgccaagagt tttgaaggtg gtcccacccc     420
gggtgccccc cgccccgaag ggcagggggtt cgccccccgg aggcaaacag agtccggaac   480
aaacaaaagg ggttaatgaa acattccccg ggcccgttag cccgggggtt cactttgtaa    540
ttgattccct                                                             550
```

```
<210> SEQ ID NO 14
<211> LENGTH: 405
<212> TYPE: DNA
<213> ORGANISM: Unknown
<220> FEATURE:
<223> OTHER INFORMATION: nuclear ribosomal internal transcribed spacer
      (nrITS) sequence

<400> SEQUENCE: 14
cggggtgtac aaagccccat acgctcgagg accggactcg gtgccgccgc tgcctttcgg        60
acccgtcccc gggggacgg agcccaacac acaagccgtg cttgaagggc agcaatgacg       120
cttcggaaca ggcatgcccc ccccgggaaa taaccagggg ggcggcaatg gtgccgtttc      180
aaaagaactc cgattgaatt tcacttgaaa ttttttgcaaa tttcaacatt aagttaatcg    240
gcattttcgc tgccgttctt tcatcgaatg cccgggaaac caaagaaaat ccgttgtttg    300 aaaggttttta aacttaatttt aggtttaatg cttcagaatg gcaatctttc agaacagagt   360
tcaataagtg tcctccggtg cgccgcggaa cccgggggca gaaag                     405
```

```
<210> SEQ ID NO 15
<211> LENGTH: 547
<212> TYPE: DNA
<213> ORGANISM: Unknown
<220> FEATURE:
<223> OTHER INFORMATION: nuclear ribosomal internal transcribed spacer
      (nrITS) sequence

<400> SEQUENCE: 15
aagcatatca aatgttgctt actggatgcc acccgccgcg acgagagacg caattctgct        60
gcgctcaaaa gccgcttggt gtgggcttgc caatccgttt tataggcgaa gtcccgcgcc      120
gatgcgggac aagaacgccc aacaccaaag cttgtgcttt gagggggtgt aaatggaccg     180
gcctccgaac aaggcatgcc cctaaaggaa ataccaaaag gggcggcaat ggtggcgttt    240
```

```
caagagattc gaatgaattc actgaaattt ctgccaattt cacactaact ttattcgcat    300
ttttgcctgc cgtttctttc attcgaatgc ccagaaaccc aagaagaatc ccatttgttt    360
gaaaagtttt tgattcttct gtctgtccct cagaacgatt tactggtatt ttacaaagaa    420
gtttgagggg gtcccccagt agccaggcca agccttgctg aggaaacgaa cgggtgctcc    480
aaaaaattag gcatggacgc tatcctcgac caggacaaaa gcccttacga taatgatcct    540
tccgcag                                                              547
```

METHOD FOR IMPROVING THE MEAN DRY SHOOT WEIGHT, MEAN DRY GRAIN WEIGHT, AND SUPPRESSING SEED-BORNE INFECTION IN A CEREAL CROP

CROSS REFERENCE TO RELATED APPLICATIONS

This application is the National Stage of International Application No. PCT/EP2015/069809, filed on Aug. 29, 2015, which claims priority to European Application No. 14182893.9, filed on Aug. 29, 2014. The contents of both applications are hereby incorporated by reference in their entirety.

FIELD OF THE INVENTION

This invention relates to the uses of isolated and cultured endophytes from wild populations of barley. In particular, the invention relates to a method for improving dry shoot weight, mean dry grain weight, and suppression of seed-borne infection in a cereal crop by inoculation with at least one or a combination of the isolated endophytes.

BACKGROUND TO THE INVENTION

Barley (*Hordeum vulgare* L.) is the world's fourth most important cereal crop, grown annually on 48 million hectares (Consultative Group on International Agricultural Research 2012), and like other food crops grown as monocultures, uses significant inputs of chemical fertilisers. According to one estimate, application of N-P-K fertilisers to barley crops worldwide will be over 4 million metric tons in 2014, which represents large economic and environmental costs, with ecosystem degradation and potential losses in biodiversity. Ways of reducing these costs whilst still maintaining acceptable yields are required if sustainable agricultural practices are to be widely adopted. Infecting barley with beneficial endophytic organisms may provide part of the solution.

As well as being economically costly, chemical crop treatments for pathogens can have severe and long-lasting negative effects on the environment and reduce biodiversity. While these chemicals can be effective in controlling pathogens in a single cropping season, infections which are transmitted vertically offer more of a challenge. Some seed-borne pathogenic microorganisms may survive seed treatments that are routinely applied. The consequent never-ending cycle of annual fungicidal crop treatments results in large cumulative economic and environmental costs. Alternative control measures using biological organisms may provide a more environmentally-friendly and long lasting solution.

Integrated Pest Management (IPM) methods can be effective in controlling some pathogens and goes some way to reducing chemical use (United Nations 2013). A more promising strategy that uses no chemicals involves exploiting the pathogen control potential offered by endophytes. Endophytes are microorganisms (bacteria, fungi and unicellular eukaryotes) which can live at least part of their life cycle inter- or intracellularly inside of plants usually without inducing pathogenic symptoms. This can include competent, facultative, obligate, opportunistic and passenger endophytes. Endophytes can have several functions and/or may change function during their lifecycle. The fungal root endophyte (*Piriformospora indica*) has been shown to supress pathogenic fungal development in barley in controlled environment experiments.

In PCT Publication No. WO 2014/121366, endophytes are described as playing a role in plant biomass production and yield in plants such as barley, and also enhances tolerance to environment stresses. In GB 2490249, compositions are described which increased seed vigour and growth. The compositions are used to coat seeds and can comprise endophytes.

Endophytes have also been shown to increase biomass in food crops, and the model endophyte *Piriformospora indica* increases grain yield (Murphy et al. 2014). *Piriformospora indica* was first isolated from the roots of desert shrubs in north-west India, and although it has been shown to increase grain yield in cool-cultivated barley under some circumstances, it may not generally be suitable for use in cooler growing conditions.

While there have been studies which examined the interactions between endophyte isolates derived from other plant genera and some important barley pathogens, there is a lack of information on the interactions between endophytes derived from wild barley species and barley cultivars. Several studies have investigated disease resistance genes derived from the wild *Hordeum vulgare* ssp. *spontaneum*, for barley diseases such as rust and spot blotch. While these genes represent significant breeding potential for cultivated barley, known diseases will evolve greater virulence as a result It is the intention of the invention to overcome at least one of the above-referenced problems.

SUMMARY OF THE INVENTION

Methods of reducing chemical crop inputs using endophyte treatments have been demonstrated. Here, the inventors' show that inoculation with a number of different fungal root endophytes isolated from wild populations of *Hordeum murinum* ssp. *murinum* increased grain yield in a nutrient-starved barley cultivar by between 15 and 29%. Furthermore, the inventors also show that inoculation with the isolates induced an increase of 11-70% in dry shoot weight in the nutrient-starved barley. The greatest increases in grain yield and dry shoot weight were achieved under the lowest nutrient input. Furthermore, it has been found that the endophytes induced significant improvements in agronomic traits for a severely drought-stressed barley cultivar grown in a controlled environment, including number of tillers, grain yield and shoot biomass. Furthermore, it was found that a greater endophyte-induced improvement in important agronomic traits in multiply-stressed plants (drought, nutrient, pathogen and heat). Only 13% of the controls survived to the end of the experiment compared with 80% of the endophyte treatments. The endophytes induced increases in the number of tillers and root and shoot biomass. The improvements were most significant for barley inoculated with a combination of all five endophytes. These results demonstrate potential for these endophytes as barley inoculants in similarly multiply-stressed farming environments. To the knowledge of the Applicant, this is the first experiment which has examined the effect of inoculating endophytes from a congeneric wild relative of barley onto abiotically and biotically stressed barley. Several of the isolates may be new species, and one particularly effective isolate has been shown to completely suppress seed-borne infections of barley. The results presented herein suggest that novel fungal root endophytes derived from a wild relative of barley may help to reduce chemical fertiliser inputs while maintaining acceptable yields. If this potential can be realised in field crops it may result in more sustainable, economically cost-effective and environmentally friendly crop treatments and a reduction in chemical fertiliser use.

A co-inoculant of ten isolates as well as two individual isolates successfully supressed the development of seed-borne fungal infections on germinated and ungerminated seed. The two most successful isolates were also the most persistent as re-emergents and may provide real potential for development as crop inoculants. All isolates were more persistent in barley exposed to light after germination. The most successful medium for supressing seed-borne infections was also the medium with the most similar composition to the soil at the sampling sites. These results suggest a direct antagonistic effect of the fungal isolates on seed-borne pathogens without the induction of plant defences.

According to the description provided herein, there is provided, as set out in the appended claims, a seed coating composition for increasing grain yield and dry shoot weight in a plant, the composition comprising a mixture of a fungal root endophyte isolated from a root of the plant and a carrier medium for application of said composition to a target seed, wherein the endophyte is characterised in having a nuclear ribosomal internal transcribed spacer (nrITS) with at least a 90% sequence identity to any one of SEQ ID NOs: 3 to 15.

According to the description provided herein, there is also provided, as set out in the appended claims, a seed coating composition for increasing tolerance to the development of seed-borne fungal infections on germinated and ungerminated seeds, the composition comprising a mixture of a fungal root endophyte isolated from a root of a plant sprouted from said seeds and a carrier medium for application of said composition to a target seed, wherein the endophyte is characterised in having a nuclear ribosomal internal transcribed spacer (nrITS) with at least a 90% sequence identity to any one of SEQ ID NOs: 3 to 15.

In one embodiment, the plant and seeds are in low-nutrient conditions. In one embodiment, the plant and seeds are in high-nutrient conditions. In one embodiment, the plant and seeds are in drought-stressed conditions. In one embodiment, the plant and seeds are in multiply-stressed conditions.

In one embodiment, the fungal root endophyte is isolated from a root of the plant *Hordeum murinum*. Preferably, the plant is *Hordeum murinum* subsp. *murinum* L. (Hmm).

In one embodiment, the fungal root endophyte is selected based on having a nuclear ribosomal internal transcribed spacer selected from any one of SEQ ID NOs 3 to 15, or variants thereof, or any combination thereof, or a combination of the variants thereof.

Preferably, the composition for increasing tolerance to the development of seed-borne fungal infections on germinated and ungerminated seeds planted in low-nutrient, drought-stressed or multiply-stressed conditions comprises the fungal root endophytes having a nuclear ribosomal internal transcribed spacer as defined by SEQ ID NO 6 or SEQ ID NO: 11, or variants thereof. In one embodiment, the composition for increasing tolerance to the development of seed-borne fungal infections on germinated and ungerminated seeds planted in low-nutrient, drought-stressed or multiply-stressed conditions comprises the fungal root endophytes having a nuclear ribosomal internal transcribed spacer as defined by SEQ ID NO 6 and SEQ ID NO: 11, or variants thereof.

In one embodiment, the composition for increasing tolerance to the development of seed-borne fungal infections on germinated and ungerminated seeds planted in low-nutrient, drought-stressed or multiply-stressed conditions comprises a combination of the fungal root endophytes having a nuclear ribosomal internal transcribed spacer as defined by SEQ ID NO 6, or a variant thereof, and one or more of the endophytes having a nuclear ribosomal internal transcribed spacer as defined by SEQ ID NO: 1, SEQ ID NO: 2, SEQ ID NO: 3, SEQ ID NO: 4, SEQ ID NO: 5, SEQ ID NO: 7, SEQ ID NO: 8, SEQ ID NO: 9, SEQ ID NO: 10, SEQ ID NO: 12, SEQ ID NO: 13, SEQ ID NO: 14 or SEQ ID NO: 15, or the variants thereof.

In one embodiment, the composition for increasing tolerance to the development of seed-borne fungal infections on germinated and ungerminated seeds planted in low-nutrient, drought-stressed or multiply-stressed conditions comprises a combination of the fungal root endophytes having a nuclear ribosomal internal transcribed spacer as defined by SEQ ID NO 11, or a variant thereof, and one or more of the endophytes having a nuclear ribosomal internal transcribed spacer as defined by SEQ ID NO: 1, SEQ ID NO: 2, SEQ ID NO: 3, SEQ ID NO: 4, SEQ ID NO: 5, SEQ ID NO: 7, SEQ ID NO: 8, SEQ ID NO: 9, SEQ ID NO: 10, SEQ ID NO: 12, SEQ ID NO: 13, SEQ ID NO: 14 or SEQ ID NO: 15, or the variants thereof.

In one embodiment, the composition for increasing tolerance to the development of seed-borne fungal infections on germinated and ungerminated seeds planted in low-nutrient, drought-stressed or multiply-stressed conditions comprises a combination of the fungal root endophytes having a nuclear ribosomal internal transcribed spacer as defined by SEQ ID NO 6 and SEQ ID NO: 11, or variants thereof, and one or more of the endophytes having a nuclear ribosomal internal transcribed spacer as defined by SEQ ID NO: 1, SEQ ID NO: 2, SEQ ID NO: 3, SEQ ID NO: 4, SEQ ID NO: 5, SEQ ID NO: 7, SEQ ID NO: 8, SEQ ID NO: 9, SEQ ID NO: 10, SEQ ID NO: 12, SEQ ID NO: 13, SEQ ID NO: 14 or SEQ ID NO: 15, or the variants thereof.

Preferably, the composition for increasing grain yield and dry shoot weight in a plant found in low-nutrient, drought-stressed or multiply-stressed conditions comprises at least one of the fungal endophyte isolates having a nuclear ribosomal internal transcribed spacer as defined by SEQ ID NO: 6, SEQ ID NO: 7 or SEQ ID NO: 8, or variants thereof. In one embodiment, the composition for increasing grain yield and dry shoot weight in a plant found in low-nutrient, drought-stressed or multiply-stressed conditions comprises a combination of the fungal endophyte isolates having a nuclear ribosomal internal transcribed spacer as defined by SEQ ID NO: 6 and SEQ ID NO: 7, or variants thereof. In one embodiment, the composition for increasing grain yield and dry shoot weight in a plant found in low-nutrient, drought-stressed or multiply-stressed conditions comprises a combination of the fungal endophyte isolates having a nuclear ribosomal internal transcribed spacer as defined by SEQ ID NO: 6 and SEQ ID NO: 8, or variants thereof. In one embodiment, the composition for increasing grain yield and dry shoot weight in a plant found in low-nutrient, drought-stressed or multiply-stressed conditions comprises a combination of the fungal endophyte isolates having a nuclear ribosomal internal transcribed spacer as defined by SEQ ID NO: 7 and SEQ ID NO: 8, or variants thereof. In one embodiment, the composition for increasing grain yield and dry shoot weight in a plant found in low-nutrient, drought-stressed or multiply-stressed conditions comprises a combination of the fungal endophyte isolates having a nuclear ribosomal internal transcribed spacer as defined by SEQ ID NO: 6, SEQ ID NO: 7 and SEQ ID NO: 8, or variants thereof.

In one embodiment, the composition for increasing grain yield and dry shoot weight in a plant found in low-nutrient, drought-stressed or multiply-stressed conditions comprises a combination of the fungal endophyte isolates having a nuclear ribosomal internal transcribed spacer as defined by SEQ ID NO: 6, or a variant thereof, and at least one or more of the endophytes having a nuclear ribosomal internal transcribed spacer as defined by SEQ ID NO: 1, SEQ ID NO: 2, SEQ ID NO: 3, SEQ ID NO: 4, SEQ ID NO: 5, SEQ ID NO: 9, SEQ ID NO: 10, SEQ ID NO: 12, SEQ ID NO: 13, SEQ ID NO: 14 or SEQ ID NO: 15, or variants thereof.

In one embodiment, the composition for increasing grain yield and dry shoot weight in a plant found in low-nutrient, drought-stressed or multiply-stressed conditions comprises a combination of the fungal endophyte isolates having a nuclear ribosomal internal transcribed spacer as defined by SEQ ID NO: 7, or a variant thereof, and at least one or more of the endophytes having a nuclear ribosomal internal transcribed spacer as defined by SEQ ID NO: 1, SEQ ID NO: 2, SEQ ID NO: 3, SEQ ID NO: 4, SEQ ID NO: 5, SEQ ID NO: 9, SEQ ID NO: 10, SEQ ID NO: 12, SEQ ID NO: 13, SEQ ID NO: 14 or SEQ ID NO: 15, or variants thereof.

In one embodiment, the composition for increasing grain yield and dry shoot weight in a plant found in low-nutrient, drought-stressed or multiply-stressed conditions comprises a combination of the fungal endophyte isolates having a nuclear ribosomal internal transcribed spacer as defined by SEQ ID NO: 8, or a variant thereof, and at least one or more of the endophytes having a nuclear ribosomal internal transcribed spacer as defined by SEQ ID NO: 1, SEQ ID NO: 2, SEQ ID NO: 3, SEQ ID NO: 4, SEQ ID NO: 5, SEQ ID NO: 9, SEQ ID NO: 10, SEQ ID NO: 12, SEQ ID NO: 13, SEQ ID NO: 14 or SEQ ID NO: 15, or variants thereof.

In one embodiment, the composition for increasing grain yield and dry shoot weight in a plant found in low-nutrient, drought-stressed or multiply-stressed conditions comprises a combination of the fungal endophyte isolates having a nuclear ribosomal internal transcribed spacer as defined by SEQ ID NO: 6 and SEQ ID NO: 7, or variants thereof, and at least one or more of the endophytes having a nuclear ribosomal internal transcribed spacer as defined by SEQ ID NO: 1, SEQ ID NO: 2, SEQ ID NO: 3, SEQ ID NO: 4, SEQ ID NO: 5, SEQ ID NO: 9, SEQ ID NO: 10, SEQ ID NO: 12, SEQ ID NO: 13, SEQ ID NO: 14 or SEQ ID NO: 15, or variants thereof.

In one embodiment, the composition for increasing grain yield and dry shoot weight in a plant found in low-nutrient, drought-stressed or multiply-stressed conditions comprises a combination of the fungal endophyte isolates having a nuclear ribosomal internal transcribed spacer as defined by SEQ ID NO: 6 and SEQ ID NO: 8, or variants thereof, and at least one or more of the endophytes having a nuclear ribosomal internal transcribed spacer as defined by SEQ ID NO: 1, SEQ ID NO: 2, SEQ ID NO: 3, SEQ ID NO: 4, SEQ ID NO: 5, SEQ ID NO: 9, SEQ ID NO: 10, SEQ ID NO: 12, SEQ ID NO: 13, SEQ ID NO: 14 or SEQ ID NO: 15, or variants thereof.

In one embodiment, the composition for increasing grain yield and dry shoot weight in a plant found in low-nutrient, drought-stressed or multiply-stressed conditions comprises a combination of the fungal endophyte isolates having a nuclear ribosomal internal transcribed spacer as defined by SEQ ID NO: 7 and SEQ ID NO: 8, or variants thereof, and at least one or more of the endophytes having a nuclear ribosomal internal transcribed spacer as defined by SEQ ID NO: 1, SEQ ID NO: 2, SEQ ID NO: 3, SEQ ID NO: 4, SEQ ID NO: 5, SEQ ID NO: 9, SEQ ID NO: 10, SEQ ID NO: 12, SEQ ID NO: 13, SEQ ID NO: 14 or SEQ ID NO: 15, or variants thereof.

In one embodiment, the composition for increasing grain yield and dry shoot weight in a plant found in low-nutrient, drought-stressed or multiply-stressed conditions comprises a combination of the fungal endophyte isolates having a nuclear ribosomal internal transcribed spacer as defined by SEQ ID NO: 6, SEQ ID NO: 7 and SEQ ID NO: 8, or variants thereof, and at least one or more of the endophytes having a nuclear ribosomal internal transcribed spacer as defined by SEQ ID NO: 1, SEQ ID NO: 2, SEQ ID NO: 3, SEQ ID NO: 4, SEQ ID NO: 5, SEQ ID NO: 9, SEQ ID NO: 10, SEQ ID NO: 12, SEQ ID NO: 13, SEQ ID NO: 14 or SEQ ID NO: 15, or variants thereof.

In one embodiment, the composition for increasing tolerance to the development of seed-borne fungal infections on germinated and ungerminated seeds planted in low-nutrient, drought-stressed or multiply-stressed conditions comprises the fungal root endophytes having a nuclear ribosomal internal transcribed spacer as defined by SEQ ID NO 6, SEQ ID NO: 8, SEQ ID NO: 13, SEQ ID NO: 14 and/or SEQ ID NO: 15, or variants thereof.

In one embodiment, the composition for increasing grain yield and dry shoot weight in a plant found in low-nutrient, drought-stressed or multiply-stressed conditions comprises at least one of the fungal endophyte isolates having a nuclear ribosomal internal transcribed spacer as defined by SEQ ID NO: 6, SEQ ID NO: 8, SEQ ID NO: 13, SEQ ID NO: 14 and/or SEQ ID NO: 15, or variants thereof.

It should be understood that the compositions described above are also suitable for increasing grain yield and dry shoot weight in a plant found in high-nutrient conditions and for increasing tolerance to the development of seed-borne fungal infections on germinated and ungerminated seeds planted in high-nutrient conditions.

In one embodiment, the concentration of the fungal endophyte isolate in the composition is between 0.001% (w/v) to 1.0% (w/v).

In one embodiment, the carrier medium is selected from water, distilled water, sterilised water, sterilised distilled water, an emulsified suspension (for example, a mixture of polyvinyl alcohol (PVA), a graft copolymer and a plasticiser), wettable powder, encapsulation of spores of the fungal endophyte(s) in alginate beads, or film-coating of seeds.

There is also provided, as set out in the appended claims, a seed coated with the composition or compositions, as described above. In one embodiment, the seed is film-coated with endophyte solution. Preferably, the film-coated seed is subsequently dried.

There is also provided, as set out in the appended claims, a seed mixed with the composition or compositions, as described above. Preferably, the carrier medium is alginate beads.

There is also provided, as set out in the appended claims, a seed encapsulated with endophyte(s)-impregnated alginate.

According to the description provided herein, there is provided, as set out in the appended claims, a method of preparing a seed having increased grain yield and dry shoot weight, the method comprising the step of inoculating the seed with a fungal root endophyte isolated from a root of a plant which produced said seed, wherein the endophyte is characterised in having a nuclear ribosomal internal transcribed spacer (nrITS) with at least a 90% sequence identity to any one of SEQ ID NOs: 3 to 15.

There is also provided, as set out in the appended claims, a method of preparing a seed with increased tolerance to the development of seed-borne fungal infections on germinated and ungerminated seeds, the method comprising the step of inoculating the seed with a fungal root endophyte isolated from a root of a plant which produced said seed, wherein the endophyte is characterised in having a nuclear ribosomal internal transcribed spacer (nrITS) with at least a 90% sequence identity to any one of SEQ ID NOs: 3 to 15.

In one embodiment, the prepared seed is planted or grown in low-nutrient conditions. In one embodiment, the plant and seeds are in drought-stressed conditions. In one embodiment, the plant and seeds are in multiply-stressed conditions.

In one embodiment of the method, the isolated fungal root endophyte is from the plant *Hordeum murinum*. Preferably, the plant is *Hordeum murinum* subsp. *murinum* L. (Hmm).

In one embodiment of the method, the step of inoculating the seed comprises applying the inoculum directly on a surface of the seed or encapsulating the seed with the inoculum.

In one embodiment of the method, the inoculum is a composition or compositions as described above.

In one embodiment of the method, the fungal root endophyte is selected based on having a nuclear ribosomal internal transcribed spacer selected from any one of SEQ ID NOs 3 to 15, or variants thereof, or any combination thereof, or a combination of the variants thereof.

In one embodiment of the method, the method for preparing a seed with increased tolerance to the development of seed-borne fungal infections on germinated and ungerminated seeds comprises inoculating the seed with a fungal root endophyte having a nuclear ribosomal internal transcribed spacer as defined by SEQ ID NO 6 or SEQ ID NO: 11, or variants thereof.

In one embodiment of the method, the method for increasing grain yield and dry shoot weight in a plant comprises inoculating the seed with at least one of the fungal endophyte isolates having a nuclear ribosomal internal transcribed spacer as defined by SEQ ID NO: 6, SEQ ID NO: 7 or SEQ ID NO: 8, or variants thereof.

In one embodiment of the method, the method for preparing a seed with increased tolerance to the development of seed-borne fungal infections on germinated and ungerminated seeds comprises inoculating the seed with a fungal root endophyte having a nuclear ribosomal internal transcribed spacer as defined by SEQ ID NO 6, SEQ ID NO: 8, SEQ ID NO: 13, SEQ ID NO: 14 or SEQ ID NO: 15, or variants thereof.

In one embodiment of the method, the method for increasing grain yield and dry shoot weight in a plant comprises inoculating the seed with at least one of the fungal endophyte isolates having a nuclear ribosomal internal transcribed spacer as defined by SEQ ID NO: 6, SEQ ID NO: 8, SEQ ID NO: 13, SEQ ID NO: 14 OR SEQ ID NO: 15, or variants thereof.

In one embodiment of the method, the concentration of the fungal endophyte isolate is between 0.001% (w/v) to 1.0% (w/v).

In one embodiment of the method, the carrier medium is selected from water, distilled water, sterilised water, sterilised distilled water, an emulsified suspension, wettable powder, encapsulation of spores of the fungal endophyte in alginate beads, or a film-coating.

In one embodiment, there is provided a seed coating composition for increasing grain yield and dry shoot weight in a plant, the composition comprising a mixture of a fungal root endophyte isolated from a root of the plant and a carrier medium for application of said composition to a target seed, wherein the endophyte is characterised in having a nuclear ribosomal internal transcribed spacer (nrITS) with at least a 90% sequence identity to any one of SEQ ID NOs: 3 to 15, wherein the variant is capable of increasing grain yield and/or dry shoot weight in a plant found in low-nutrient, drought-stressed or multiply-stressed conditions.

In one embodiment, there is also provided a seed coating composition for increasing tolerance to the development of seed-borne fungal infections on germinated and ungerminated seeds, the composition comprising a mixture of a fungal root endophyte isolated from a root of a plant sprouted from said seeds and a carrier medium for application of said composition to a target seed, wherein the endophyte is characterised in having a nuclear ribosomal internal transcribed spacer (nrITS) with at least a 90% sequence identity to any one of SEQ ID NOs: 3 to 15, wherein the variant is capable of increasing tolerance to the development of seed-borne fungal infections on germinated and ungerminated seeds.

In one embodiment, there is provided a method of preparing a seed having increased grain yield and dry shoot weight, the method comprising the step of inoculating the seed with a fungal root endophyte isolated from a root of a plant which produced said seed, wherein the endophyte is characterised in having a nuclear ribosomal internal transcribed spacer (nrITS) with at least a 90% sequence identity to any one of SEQ ID NOs: 3 to 15, wherein the variant is capable of increasing grain yield and/or dry shoot weight in a plant found in low-nutrient, drought-stressed or multiply-stressed conditions.

In one embodiment, there is provided a method of preparing a seed with increased tolerance to the development of seed-borne fungal infections on germinated and ungerminated seeds, the method comprising the step of inoculating the seed with a fungal root endophyte isolated from a root of a plant which produced said seed, wherein the endophyte is characterised in having a nuclear ribosomal internal transcribed spacer (nrITS) with at least a 90% sequence identity to any one of SEQ ID NOs: 3 to 15, wherein wherein the variant is capable of increasing tolerance to the development of seed-borne fungal infections on germinated and ungerminated seeds.

Definitions

In the specification, the term "ruderal" should be understood to mean a plant species that is first to colonize disturbed lands. The disturbance may be natural or a consequence of human activity.

In the specification, the term "isolated endophyte" should be understood to mean fungal emergents from root pieces of, for example, *Hordeum murinum* subsp. *murinum* L., which have been inoculated onto culture medium and subsequently individually subcultured from single spores or mycelia to obtain a single uncontaminated organism.

In the specification, the term "variants thereof", should be understood to mean polynucleotides sequences which are substantially identical to the full nuclear ribosomal internal transcribed spacer of an isolated endophyte. Thus, for example, the term should be taken to include polynucleotides that are altered in respect of one or more nucleic acids. Preferably such alterations involve the insertion, addition, deletion and/or substitution of 15 or fewer nucleic acids, more preferably of 12 or fewer, even more preferably of 9 or fewer, most preferably of 3 or 6 nucleic acids only. The variant may have conservative nucleic acid changes, wherein the nucleic acid being introduced does not change the structure or activity of the translated nucleic acid sequence. Typically, any sequence which has been altered by substitution or deletion of catalytically-important nucleic acids will be excluded from the term "variant". Generally, the variant will have at least 70% sequence identity, preferably at least 80% sequence identity, more preferably at least 90% sequence identity, and ideally at least 95%, 96%, 97%, 98% or 99% sequence identity with the wild-type nuclear ribosomal internal transcribed spacer of the isolated endophyte as depicted in SEQ ID NOs 3 to 15; and wherein the variant is capable of increasing grain yield and/or dry shoot weight and/or tolerance to the development of seed-borne fungal infections on germinated and ungerminated seeds.

In the specification, the term "film-coated" should be understood by those skilled in the art to mean a thin polymer-based coat applied to a solid form such as a seed or a tablet. The coating can be aqueous or non-aqueous based. The thickness of such a coating is usually between 20-100 μm. Film coating formulations generally comprise a polymer (for example, cellulose derivatives or acrylic polymers and copolymers such as•Hypromellose, •Hydroxyethyl cellulose, Hydroxyethylmethyl cellulose, Carboxymethylcellulose, •Hydroxypropyl cellulose, Polyethylene glycol, •Ethylcellulose, •Hypromellose phthalate, •Polyvinyl acetate phthalate, •Cellulose acetate phthalate, •Polymethacrylates, •Shellac), a plasticiser (such as, for example, glycerol, propylene glycol, PEG (Polyethylene glycol), phthalate esters, dibutyl sebacete, citrate esters, triacetin, castor oil, acetylated, monoglycerides, fractionated coconut oil) and a carrier (generally, water or organic solvents such as alcohols, ketones, esters and chlorinated hydrocarbons). Water is the preferable carrier.

In the specification, the term "multiply-stressed" should be understood to mean where plants have been stressed by a number of factors such as one or more of drought, nutrient-depleted or nutrient-poor soils, pathogen infection and heat.

BRIEF DESCRIPTION OF THE DRAWINGS

The invention will be more clearly understood from the following description, given by way of example only, with reference to the accompanying drawings, in which.

DETAILED DESCRIPTION

Figure 1:
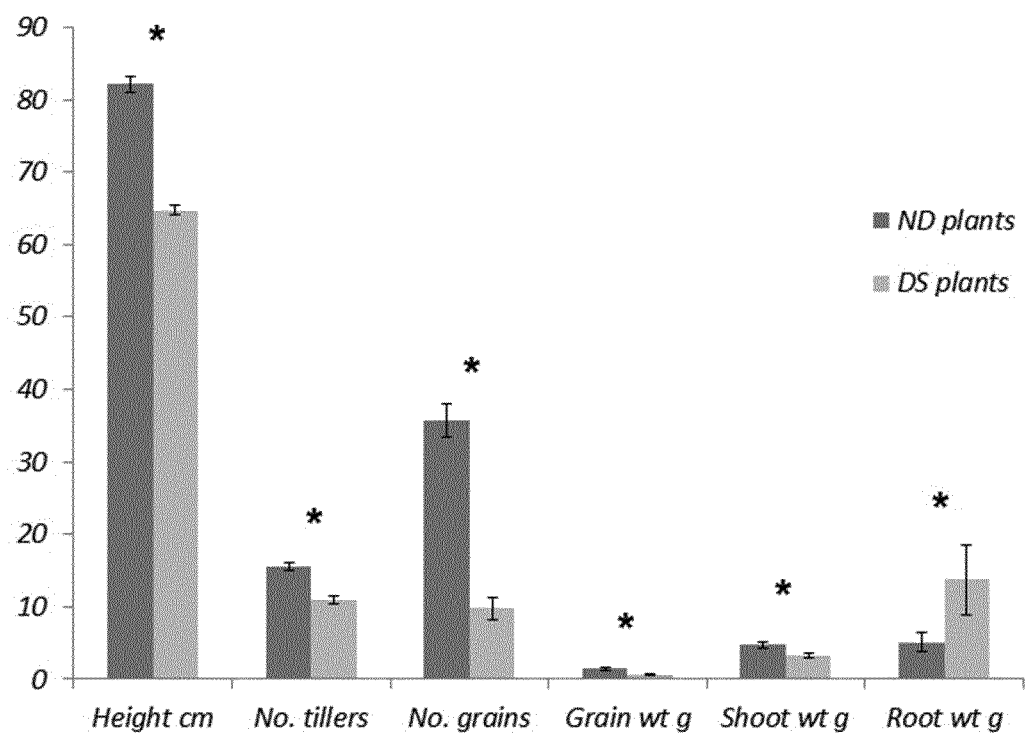
FIG. 1 is a graph depicting the mean overall harvest parameters for all treatments±S.E. for well-watered (ND) and drought-stressed (DS) plants of barley H. vulgare cultivar Propino. Significant differences (P<0.05) between ND and DS are indicated with *.

*Hordeum murinum* subsp. *murinum* L. (Hmm) is an annual grassy species and a ruderal of roadsides, rough grassland and waste places. As the species generally grows in stressed environments, it may have evolved symbiotically-conferred stress tolerance associated with endophyte infection, and these endophytes may help the plants to grow in nutrient-stressed conditions. Endophytes isolated from Hmm may have the potential to benefit cultivated barley in low-nutrient, drought-stressed and multiply-stressed conditions.

Materials and Methods

Whole plants of Hmm were collected from ten urban and suburban populations from within a ten km radius of a point centred at 53.39602N, 6.21632W (O 18636 39912) in June-July. Root samples were only collected from populations with greater than ten individuals, and a minimum of ten plants per population was collected. Environmental variables were recorded at the time of collection and included: soil pH, soil salinity (measured as osmotic potential in bars), soil moisture content, height of plant, Zadoks growth stage (Zadoks et al. 1974) and plant health. Plant health was scored on a five point scale, with a score of five indicating large plants of excellent health with no apparent disease or physiological stress symptoms and a score of zero indicating plants with severe disease symptoms. The overall vegetation type and soil type for each site was assessed using a numerical equivalent. For vegetation type: 1=a site without soil and with no other vegetation (for example the edge of a roadside kerb), 2=an open site with short grass, 3=an open site with short weedy vegetation, 4=a site with shading deciduous trees and short grass, 5=a site at the base of a wall with no other vegetation. For soil type: 1=a light sandy silt, 2=a light sandy loam, 3=a dark clay loam with few stones.

Roots were separated from whole plants and surface-sterilised in 5% NaClO for 15 minutes then rinsed five times with sterile water. Thirteen root pieces of 5 mm length from each plant were inoculated onto culture plates of malt extract agar (Fluka 38954 modified MEA, Vegitone) and incubated in the dark at 25° C. for 28 days. Dishes were inspected daily and those containing root pieces with surface fungal growth were discarded. Emergent endophytes were removed and subcultured on the same media in the dark at 25° C. for a further 14 days. Thirteen endophytes were selected for the experiments from a total of 106 isolates. These were selected on the basis of strong growth, the early appearance and quantity of conidia, distinctive morphology representative of the major types and a lack of bacterial contaminants.

For the DNA analysis, 20 mg of fungal material was scraped from the agar surface and placed into shaker tubes. DNA was extracted using a Qiagen DNeasy mini kit, following the Qiagen protocol, producing 200 μl of DNA extract for each isolate. PCR was carried out on the DNA extracts using the nuclear ribosomal DNA (rDNA) internal transcribed spacer (ITS) primers ITS1 (forward primer) (SEQ ID NO: 1-5' TCCGTAGGTGAACCTGCGG 3') and ITS4 (reverse primer) (SEQ ID NO: 2-5' TCCTCCGCTT-ATTGATATGC 3'). PCR products were cleaned up using Exonuclease (New England Biolabs) and Shrimp Alkaline Phosphatase (ExoSAP; Roche). Purified PCR products underwent cycle sequencing using the reverse ITS4 primer (4 pmol) in separate reactions with the ABI BigDye 3.1 kit (Foster City, Calif.). The products were further purified using a BigDye XTerminator purification kit and protocol. DNA was sequenced using an Applied Biosystems 3130xL Genetic Analyzer. The full nuclear ribosomal internal transcribed spacer (nrITS) sequences for the thirteen endophyte isolates can be found as SEQ ID NOs: 3 to 15.

The nrITS DNA region is recognised and accepted in the field as the best region for taxa delimitation in fungi, and thus is a good marker to define the endophytes within the scope of the invention. Between the 13 sequences provided herein, there is a minimum 90% sequence similarity, which is a criterion for covering related endophyte isolates.

The isolate sequences were compared with GenBank accessions using the Basic Local Alignment Search Tool (BLAST), and identified using morphological and DNA characters. The nearest named matches from BLAST were investigated using internet searches for any reported human or plant toxicity.

112 taxa of fungi were identified based on the ITS sequence similarity. Representatives were found from 8 orders, 12 families, and 18 genera (Murphy et al. 2015b). Within this group, only 34 isolates (30% of the total) could be confidently assigned to a species, and 23 of the isolates (21% of the total) had no significant match to anything deposited in GenBank (based on <85% sequence similarity). For the six reconstructed phylogenies for identified genera in each fungal order, a mean 53% of recovered sequences did not cluster in the same clade with the selected GenBank accessions. In particular, over half of the recovered sequences in the Hypocreales, Pleosporales and Xylariales phylogenies clustered as separate clades outside of the main generic clade. These results suggest a high proportion of novel fungi, with 28% not assigned to a known fungal order. This includes 3 endophytes that have been shown to significantly improve agronomic traits in cultivated barley. This study has, therefore, revealed a profound diversity of fungal root endophytes in a single wild relative of barley. Extrapolating from this the study highlights the largely unknown, hugely diverse, and potentially useful resource of crop wild relative endophytes.

Five of the most commonly used fungal culture media were selected: OXOID™ Corn meal agar (CM0103); OXOID™ Czapek Dox liquid agar medium, modified (CM0095), to which was added 16 g/L of Sigma Agar select A-5054 38954; Malt extract agar modified, Vegitone (Fluka 38954); Potato dextrose agar (Applichem A5838,0500) and OXOID™ Sabouraud maltose agar (CM0541) (Table 1). The powdered media were mixed to half-strength of the manufacturers' recommendations using pure water then boiled and sterilised by autoclaving.

TABLE 1

Nutritional and additive profiles for each medium, amounts are per culture dish.

| Medium | pH | Carbon source (g) | Nitrogen source (g) | Agar content (g) | Other additives (g) |
|---|---|---|---|---|---|
| Corn meal extract | 6.0 | From whole maize/ Sugars = 0.04 g, N content = 0.003 g | | 0.1 g | |
| Czapek | 6.8 | Sucrose/ | NaNO3/ | 0.1 g | KCl/0.003 g, |
| Dox | | 0.2 g | 0.013 g | | MgC3H9O6P/ 0.0003 g, FeSO4/ 0.00007 g, K2SO4/ 0.0023 g |
| Malt extract | 4.7 | Maltose/ 0.087 g | Vegetable peptone/ 0.005 g | 0.1 g | Dextrin/0.02 g |
| Potato dextrose | 5.6 | Glucose/ 0.3 g | Potato extract/ 0.027 g | 0.1 g | |
| Sabouraud | 5.6 | Maltose/ 0.27 g | Mycological peptone/ 0.067 g | 0.1 g | |

Seed-Borne Infection

The ten selected endophyte isolates of SEQ ID NOs: 3 to 12 were subcultured from single spores and incubated for 28 days on each of the five media. 40 mg of fungal material (conidia/spores and mycelia) from each of the ten isolates were mixed together by magnetic bar stirring in 100 ml of sterile water for 3 hours at 35° C. Fifteen unblemished and sterilised seeds of the barley cultivar 'Propino' (Goldcrop Seeds, Cork, Ireland) were surface-sown on separate culture dishes of each medium and inoculated with 250 µl of the fungal mixture. The inoculant was applied directly onto each seed. A further set of 15 culture dishes for each medium, containing no seeds, were inoculated with 250 µl of the endophyte solution. As a control, 15 culture dishes for each medium were surface sown with seed and no inoculant applied.

All dishes were incubated in the dark at 25° C. until the coleoptile had emerged at Zadoks growth stage seven and then half of the culture dishes were moved to a well-lit environment (250 µmol m$^2$ s$^{-1}$ with an eight hr photoperiod at 25° C.). All dishes were incubated for a further 21 days. The presence/absence of the inoculant or seed-borne fungi was recorded for each culture dish. Roots were harvested from each culture dish and surface sterilised by immersing in 5% NaClO for 15 mins and rinsing 5 times with sterile water. From each seedling, ten root pieces of 10 mm length were inoculated onto the original source media and incubated at 25° C. for 21 days. Any emergent endophytes were identified by examination of the mycelia and conidia.

To test for interactions between seed-borne fungi on ungerminated seed and the endophyte isolates, 30 sterilised seeds were submerged beneath the agar in dishes for each medium and half (15) were inoculated with the endophyte solution (the seeds will not germinate in the anoxic conditions). Culture dishes were incubated at 25° C. for 21 days. The presence/absence of the inoculant or seed-borne fungi was recorded for each culture dish.

The experiment was repeated for individual inoculations of isolates to determine what effect each endophyte isolate had on seed-borne barley infections. For each medium, 15 culture dishes of surface-sown (which will germinate) and submerged seed were inoculated with each individual endophyte. As a control, 15 culture dishes for each medium were surface and submerged-sown with the seed and no inoculant applied. The culture dishes were then incubated as before and the presence/absence of the inoculant or seed-borne fungi was recorded for each culture dish. Roots were harvested and processed as described above, and any emergent endophytes were identified by examination of the mycelia and conidia.

When the results from the above procedures were known, a simple in vitro antibiosis test was set up, whereby the endophyte isolate with the greatest seed-borne infection suppression was inoculated onto 5 culture dishes of half-strength Sabouraud medium which had a 10 mm$^2$ culture of *Gaeumannomyces graminis* var. *tritici* (Ggt) (GenBank accession number KF018415) already growing on it. This was done to test the effectiveness of the endophyte isolate in supressing one of the most serious horizontally transmitted barley pathogens, rather than vertically as for the seed-borne infections.

To determine the role of pH, nitrate and sodium cations in the suppression of seed-borne infection, the pH of the medium with the highest (Czapek Dox, pH=6.8) was adjusted to that of the medium with the lowest (Malt extract, pH=4.7) and vice versa. Another adjusted medium was prepared by adding the same concentration of NaNO$_3$ contained in Czapek Dox to the Malt extract medium. 20 seeds were then sown onto each of the adjusted media and inoculated with the most suppression-effective endophyte (determined from the first part of the experiment). Culture dishes were incubated as before.

Effect on Mean Dry Grain Weight and Dry Shoot Weight

The ten fungal root endophytes isolated from wild populations of Hmm, as described above for SEQ ID NOs: 3 to 12, were prepared from single spores, following Murphy et al. (2014).

Untreated seeds of the barley cultivar 'Propino' were supplied by Goldcrop Seeds, Cork, Ireland. Propino is an established British cultivar (Cross: (Quench x NFC Tipple)) which is widely grown in Ireland. It is suitable for both malting and feed, with very high yield potential and good resistance to both *Rhynchosporium* and net blotch (*Pyrenophora teres*).

Seeds were surface-sterilised by soaking in 5% NaClO for 15 min, rinsing three times with 70% ethanol and then rinsing five times with pure water. The growth compost consisted of sterilised coarse vermiculite to which was added 1.43 g P4 broadleaf water absorbing polymer granules (Agricultural Polymers International Ltd.) per 1.5 litre of vermiculite. The compost was dry mixed, moistened with tap water and placed into 1.5 litre washed and sterilised (soaked for 2 hours in 5% NaClO then rinsed×5 with tap water) plastic pots.

For each inoculation treatment (including a control), fifty seeds of barley, five per pot, were sown at 30 mm depth and inoculated with one of the ten endophytes. The inoculant solution was prepared by mixing 10 mg of each fungal culture with 5 ml of sterilised and deionised water and stirring with a magnetic bar for 2 hr at 35° C. 250 µl of the solution was directly inoculated onto each seed. For the controls, the seeds were inoculated with 250 µl pure water.

The environmental settings were programmed to produce a 13 hr photoperiod at a compost surface illumination of 210 µmol·m$^{-2}$ s$^{-1}$, a photoperiod temperature of 15° C., a dark period temperature of 8° C. and 70% relative humidity. The photoperiod was extended by two hours at 21 days from date of sowing and to 17 hr at day 42. The temperature was raised by 2° C. at day 21 and by a further 2° C. at day 42.

Three agar-filled covered culture dishes containing 5 sterilised seeds of each cultivar of barley were kept in the growth chambers during the experimental period to monitor any seed-produced endophyte growth. Further, agar-filled covered culture dishes containing 5 split sterilised and unsterilised seeds of each cultivar of barley were incubated in the dark at 25° C.

The seedlings were thinned to 3 plants per pot when the last seedling in each pot had reached Zadoks stage 10 (first leaf unfolded). The final planting density was 106 plants m$^2$, which is within the normally recommended field planting density for barley. Soil moisture was measured daily using a Delta-T Devices HH2 WET sensor kit (delta-t.co.uk) and soil moisture content at a depth of 50 mm was maintained at 25%±10% (representing field capacity) from germination until 14 days after germination by watering with tap water. Plants were given a liquid fertiliser (Bayer Phostrogen®) at each watering after germination. Half of the plants were given lower nutrient inputs (LO) and half were given higher (HI) nutrients; for the HI nutrient treatments, the total nutrient input per plant was: ammoniacal N=0.013 g, ureic N=0.078 g, Total N=0.09 g, P=0.057 g, K=0.146 g, Mg=0.01 g, S=0.02 g, Ca=0.01 g and traces of Boron, Copper, Iron, Manganese, Molybdenum and Zinc; for LO nutrient treatments, the total nutrient input per plant was halved for all elements. The HI treatment contained the recommended input of fertiliser for hydroponically-grown plants (2 g Bayer Phostrogen® per 5 litres water, see phostrogen.co.uk/gardenerscorner/guides. However, even for the HI treatment the amounts of N, P and K were much less than the recommended inputs (lower by 18%, 44% and 42% respectively) for barley growing on low-nutrient soils (teagasc.ie/crops/winter/fertilisers/winter_cereals fertiliser requirements.pdf). To ensure healthy growth, the plants were sprayed with plain water once a week and the aggregate washed through with plain water monthly to remove any accumulation of nutrient salts. The growing compost was kept moist and the total water input was 6.1 litres per plant.

The number of days to reach selected Zadoks stages was recorded for each plant. Plants were grown for 98 days (14 weeks) from date of sowing, by which time over 75% of plants had reached full maturity, then harvested and processed over a period of 2 days. Pots were selected for processing in random order. All of the grains had at least reached the soft dough stage (Zadoks stage 85). Measurements were made for each plant of fresh and dry weights of grains, shoots and roots; mean height of heads to tip of highest grain; number of heads; number of tillers and number of grains per head. All plant parts were separately dried in ovens for 3 days at 65° C. before dry weights were measured.

At the end of the experiment and before drying the roots, four 5 mm pieces of mid-section root from each plant were surface-sterilised and incubated on half-strength MEA at 25° C. in the dark to test for endophyte presence.

For Additional Experiments Relating to SEQ ID NOs: 6, 8 and 13 to 15 Only

The five fungal root endophytes were isolated from wild populations of Hmm in Ireland and DNA from the nuclear ribosomal Internal Transcribed Spacer (nrITS) region was sequenced, as previously described (Murphy et al. 2014). The isolate sequences SEQ ID NO: 6, SEQ ID NO: 8, SEQ ID NO: 13, SEQ ID NO: 14 and SEQ ID NO: 15 were compared with GenBank accessions using the Basic Local Alignment Search Tool (BLAST), and identified using morphological and DNA characters. The nearest named matches from BLAST were investigated using internet searches for any reported human or plant toxicity and for any extant patents for utilisation of the organisms. Pure cultures of the isolates were prepared from single spores, following Murphy et al. (2014).

Untreated seeds of the barley cultivar 'Propino' (supplied by Goldcrop Seeds, Cork, Ireland) were used. Seeds were surface-sterilised by soaking in 5% NaClO for 15 min, rinsing three times with 70% ethanol and then rinsing five times with pure water. The growth compost of John Innes No. 3 formulation (Westland Horticulture Limited, garden-health.com) was placed into 120×1.5 litre washed and sterilised (soaked for 2 hours in 5% NaClO then rinsed×5 with tap water) plastic pots. For each inoculation treatment (including a control), fifty seeds of barley, five per pot, were sown at 30 mm depth and inoculated with one of the five endophytes. The inoculant solution was prepared by mixing 10 mg of each fungal culture with 5 ml of pure water and stirring with a magnetic bar for 2 hr at 35° C. 250 µl of the solution was directly inoculated onto each seed. For the controls, the seeds were inoculated with 250 µl pure water.

The environmental settings were programmed to produce a 14 hr photoperiod at a compost surface illumination of 220 µmol·m$^{-2}$ s$^{-1}$, a photoperiod temperature of 23° C. reducing to 12 C in the dark period and a constant 70% relative humidity.

Three covered culture dishes containing 5 sterilised seeds on Malt Extract Agar (Fluka 38954) were kept in the growth chamber during the experimental period to monitor any seed-produced endophyte growth. Further, agar-filled covered culture dishes containing 5 split sterilised and unsterilised seeds of each cultivar of barley were incubated in the dark at 23° C.

The seedlings were thinned to three plants per pot seven days after germination. Soil moisture was measured daily using a Delta-T Devices HH2 WET sensor kit (delta-t.co.uk) and soil moisture content at a depth of 50 mm was maintained at 25%±10% (representing field capacity) from germination until 14 days after germination by watering with tap water. After this period, half of the plants were given lower water inputs (LO) and half were given higher (HI) water input; for the HI treatments, the soil moisture content was maintained at approximately 25% as before; for LO treatments, pots were only watered when the soil moisture content was between 2% and 5%, when the pots were watered until soil moisture content was again at field capacity (~25%). All pots were given a liquid fertiliser (Bayer Phostrogen®) at each watering of the LO treatment (total nutrient input per pot was: ammoniacal N=0.2364 g, ureic N=1.418 g, Total N=1.654 g, P=1.04 g, K=2.646 g, Mg=0.172 g, S=0.357 g, Ca=0.169 g and traces of Boron, Copper, Iron, Manganese, Molybdenum and Zinc).

The number of days to reach selected Zadoks stages (Zadoks et al. 1974) was recorded for each plant. Plants were grown for 98 days (14 weeks) from date of sowing, then harvested and processed over a period of 2 days. Pots were selected for processing in random order. All of the grains had at least reached the soft dough stage (Zadoks stage 85). Measurements were made for each plant of fresh and dry weights of grains, shoots and roots; mean height of heads to tip of highest grain; number of heads; number of tillers and number of grains per head. All plant parts were separately dried in ovens for 3 days at 65° C. before dry weights were measured.

At the end of the experiment and before drying the roots, four 5 mm pieces of mid-section root from each plant were surface-sterilised and incubated on half-strength Malt Extract Agar at 25° C. in the dark to test for endophyte presence.

General Materials and Methods

In order to determine if the endophyte isolates could be transmitted vertically and/or horizontally, 30 surface-sterilised seeds from plants inoculated with endophyte isolates 040901(3) (having an nrITS of SEQ ID NO: 6) and 040906 (4) (having an nrITS of SEQ ID NO: 8) were sowed into fresh compost, and 30 new seeds into the compost which contained the plants previously inoculated with these two isolates. Seedlings were harvested at Zadoks growth stage 12 (second leaf 50% emerged) and the roots processed as before to check for emergent endophytes.

Data analysis by ANOVA was performed using the Data Analysis modules provided by Microsoft Excel 2010®.

Results

The nrITS sequences obtained from analysis of the endophyte isolates were used to search for similar sequences in GenBank using the BLAST search tool. Closest matches ranged from 93.8% to 100% identical, with a mean pairwise identity match of 97.3% (Table 2). If criteria of a less than 97% match was used to indicate possible new species, then four of the endophyte isolates may be new species. The search results indicated that the ten endophyte isolates as defined by SEQ ID NOs: 3 to 12 represented five different fungal orders (Capnodiales, Chaetothryiales, Eurotiales, Hypocreales and Pleosporales). The generic identity obtained from GenBank was confirmed by morphological examination.

TABLE 2

Nearest BLAST search matches for ITS sequences obtained from ten endophyte isolates derived from wild populations of wall barley. Toxicity refers to known (+) human or plant toxicity.

| Isolate | Nearest BLAST match | % Identical | Toxicity |
|---|---|---|---|
| 040207(3) | *Paecilomyces marquandii* JQ013003 | 98.6 | |
| 040406(3) | *Viridispora alata* JF832678 | 94 | |
| 040605(2) | *Cladosporium* sp. GQ169491 | 99.6 | |
| 040901(3) | *Penicillium brevicompactum* EU587331 | 94.8 | + |
| 040902(5) | *Pyrenochaeta unguis-hominis* JX966641 [4] | 98 | + |
| 040906(4) | Uncultured *Metarhizium* KC797571 | 95.5 | |
| 040909(5) | Uncultured fungus FJ820798 (*Penicillium*?) | 93.8 | |
| 041004(5) | *Exophiala oligosperma* JN655630 | 100 | + |
| 041008(5) | *Penicillium brevicompactum* FJ884117 | 99.6 | + |
| 041010(3) | *Penicillium* sp. FR822844 | 99.4 | |

All of the Hmm sampling sites were characterised by a relatively high soil salinity (mean=1.37 bars), high soil pH (mean 7.7) and low soil moisture content (mean 10.7%), with four sites having no measurable soil moisture (Table 3). There was a positive correlation between the number of emergent endophytes from the roots of Hmm and a light sandy silt soil (Pearson's product moment correlation, p<0.05), a low (or unmeasurable) soil moisture content (p<0.05) and high salinity (p<0.05). Location 9 had significantly more endophyte emergents than the other locations (single factor ANOVA, $F_{1,16}$=61.9, p<0.01).

TABLE 3

Environmental and plant variables for collection sites. Mean height is ± standard error (n = 10).

| | | Soil measurements | | | Plant measurements | | | | |
|---|---|---|---|---|---|---|---|---|---|
| Loc. | pH | Moisture content % | Salinity* | Soil type | Mean height cm | Zadoks stage | Health | Veg. type | No. Endo. |
| 1 | 7.2 | 28.2 | 1.28 | 3 | 63 ± 0.99 | 61 | 5 | 4 | 5 |
| 2 | 7.3 | 32.2 | 1.46 | 2 | 38 ± 4.34 | 66 | 2 | 2 | 10 |
| 3 | 7.8 | 9.1 | 1.18 | 1 | 38 ± 2.96 | 61 | 2 | 1 | 6 |
| 4 | 8.0 | 13.4 | 1.41 | 1 | 51 ± 3.68 | 61 | 5 | 2 | 12 |
| 5 | 7.6 | 0 | 1.22 | 1 | 46 ± 4.07 | 66 | 1 | 3 | 16 |
| 6 | 7.9 | 4.4 | 1.39 | 1 | 29 ± 2.49 | 59 | 4 | 5 | 7 |
| 7 | 7.9 | 0 | 1.45 | 1 | 44 ± 2.74 | 61 | 3 | 3 | 15 |
| 8 | 7.7 | 19.5 | 1.26 | 3 | 20 ± 1.78 | 61 | 5 | 4 | 1 |
| 9 | 7.7 | 0 | 1.49 | 1 | 46 ± 3.98 | 61 | 5 | 3 | 23 |
| 10 | 7.7 | 0 | 1.51 | 1 | 26 ± 3.59 | 66 | 3 | 3 | 14 |
| MEAN | 7.7 | 10.7 | 1.37 | | 40.1 | 62.3 | 3.5 | | 11 |

*Salinity is Osmotic Pressure in bars

The appearance of seed-borne infections on culture dishes co-inoculated were compared with a combined treatment of all ten endophytes as defined by SEQ ID NOs: 3 to 12. The control dishes with no inoculant for both germinated and ungerminated seeds had some typical seed-borne fungal infections, including species of *Cochiolobus*, *Colletotrichum*, *Fusarium*, *Pyrenophora* and *Rhynchosporium*. The fungi were identified by microscopic examination, mycelial morphology and growth characteristics. None of these organisms appeared on the inoculated dishes with or without seeds. Six endophyte isolates appeared at least once, and the endophyte isolate 040901(3) (having an nrITS of SEQ ID NO: 6) was the only endophyte present on all media for germinated and ungerminated seed.

The appearance of seed-borne infections on the culture dishes inoculated were also compared with individual endophytes (Table 5). When present on a medium, the endophyte or seed-borne fungus occurred on every culture dish. Two endophyte isolates, 040901(3) (having an nrITS of SEQ ID NO: 6) and 041008(5) (having an nrITS of SEQ ID NO: 11), gave 100% suppression of seed-borne barley infections on both germinated and ungerminated seed. This represents significantly greater suppression of seed-borne infections than all of the other endophytes (single factor ANOVA, $F_{1,28}=42.7$, $p<0.01$). These two endophytes were isolated from light sandy silty soils with 0% moisture content. The most successful medium for supressing seed-borne infections was Czapek Dox with 75% of culture dishes containing no seed-borne infections; the least successful was Malt extract agar with 50% containing no seed-borne infections.

TABLE 5

Presence or Absence of individually inoculated endophyte isolate (F) and seed-borne fungus (B) on growth medium containing germinated (Seedling) and un-germinated (Seed) seeds of barley, incubated at 25° C. for 21 days after inoculation. When present on a medium, F or B occurred on every culture dish (n = 15).

| | Growth Medium | | | | | | | | | | |
|---|---|---|---|---|---|---|---|---|---|---|---|
| | Corn Meal | | Czapek Dox | | Malt Extract | | Potato dextrose | | Sabouraud | | |
| Isolate | Seedling | Seed | Seedling | Seed | Seedling | Seed | Seedling | Seed | Seedling | Seed | Totals |
| 040207(3) | F | F | F | F | FB | FB | F | F | F | F | 10F, 2B |
| 040406(3) | B | B | F | F | B | B | B | F | F | F | 5F, 5B |
| 040605(2) | B | F | F | B | F | F | B | F | B | B | 5F, 5B |
| *040901(3) | F | F | F | F | F | F | F | F | F | F | 10F* |
| 040902(5) | F | B | F | F | B | B | B | B | F | FB | 5F, 6B |
| 040906(4) | F | F | F | B | F | B | F | F | F | FB | 8F, 3B |
| 040909(5) | B | B | F | B | B | B | F | B | F | FB | 4F, 7B |
| 041004(5) | F | F | B | F | F | F | F | F | B | F | 8F, 2B |
| *041008(5) | F | F | F | F | F | F | F | F | F | F | 10F* |
| 041010(3) | F | F | F | F | B | B | F | F | F | F | 8F, 2B |
| Totals | 7F, 3B | 7F, 3B | 9F, 1B | 7F, 3B | 6F, 5B | 5F, 6B | 7F, 3B | 8F, 2B | 8F, 2B | 9F, 4B | 73F, 32B |

Items marked with *indicate no seed-borne infections present on any medium for seed and seedling.

In all cases of suppression there was still no appearance of seed-borne infections 42 days after inoculation of the seed with the endophyte(s).

When the endophyte isolate with the greatest seed-borne infection suppression, 040901(3) (having an nrITS of SEQ ID NO: 6), was inoculated onto a culture dish containing the culture of Ggt, the isolate completely stopped any further growth of the Ggt culture after it had made contact with the leading edge of Ggt, which eventually became overgrown with 040901(3) (having an nrITS of SEQ ID NO: 6).

The persistence of the individual endophytes after inoculation of the seeds with either the mixture of ten endophytes as defined by SEQ ID NOs: 3 to 12 or individual inoculation were tested by culturing root pieces from the resultant seedlings and identifying the emergent endophytes. For the co-inoculation with all ten endophytes as defined by SEQ ID NOs: 3 to 12 (Table 6), there was only one emergent endophyte from 85% of root pieces. For the ten root pieces, Sabouraud medium had the most emergent endophytes with six (60%), and the Potato dextrose and Czapek Dox had the least emergents with three. Of the 10 endophyte components of the inoculant, six different endophytes emerged. The endophyte isolate 040906(4) (having an nrITS of SEQ ID NO: 8) occurred most frequently (5 times), but with never more than 30% culture dish cover. The culture dishes that were moved to a well-lit environment had significantly more emergents than the culture dishes kept in the dark (single factor ANOVA, $F_{1,28}=7$, $p<0.05$). For the individual endophyte inoculants (Table 7), the endophyte isolate 040901(3) (having an nrITS of SEQ ID NO: 6) emerged from 48% of all root pieces, with 041008(5) (having an nrITS of SEQ ID NO: 11) the next most frequent with 34%.

When the pH of the Czapek Dox medium was adjusted to that of the Malt extract medium, and vice versa, there was still 100% suppression of seed-borne infections by the 040901(3) (having an nrITS of SEQ ID NO: 6). The addition of NaNO$_3$ to the Malt extract (pH 4.7) resulted in slower growth and development of the endophyte, but eventually resulted in complete suppression of seed-borne infections.

When the vertical transmission potential of the endophytes were tested, it was found that only one root piece (3%) produced the emergent endophyte 040901(3) (having an nrITS of SEQ ID NO: 6). For the horizontal transmission test, three root pieces (10%) produced emergents of 040901 (3) (having an nrITS of SEQ ID NO: 6). The endophyte isolate 040906(4) (having an nrITS of SEQ ID NO: 8) did not emerge from any root pieces. In a separate experiment, fully-mature barley plants showed no ill-effects compared to the control after inoculation with either one or a combination of endophyte isolates (see Table 8).

The results presented herein clearly demonstrate that a co-inoculant of 10 fungal root endophyte isolates as defined by SEQ ID NOs: 3 to 12, as well as two individual isolates, derived from a wild barley species effectively suppressed the development of seed-borne infections in a barley cultivar. The results are important because the seed-borne infections that emerge from control seeds with no inoculant (probably due to the seeds being untreated as supplied) are some of the most devastating pathogens of barley. Therefore, this indicates that where suppression of seed-borne infections occurred, up to five potential pathogens have been suppressed. This is particularly interesting for the ungerminated seeds as it suggest a direct antagonistic effect of the endophyte(s) on seed-borne pathogens without the induction of

TABLE 6

Identity and mean proportion (±S.E.) of culture dish covered (Id/Prop) of emergent endophytes for ten root cultures, of the barley variety 'Propino' co-inoculated with a mixture of ten endophytes on one of five media for seeds cultured at 25° C. in the dark for 28 days or moved to the light seven days after inoculation (n = 15).

| Medium | Conditions | Id/Prop | Id/Prop | Id/Prop |
|---|---|---|---|---|
| Corn Meal | Dark | 040207(3)/20% ± 2.8 | | |
| | Moved to light | 040605(2)/30% ± 3.9 | 040901(3)/20% ± 2.0 | 040207(3)/10% ± 2.2 |
| Czapek Dox | Dark | 040902(5)/30% ± 3.9 | 040906(4)/10% ± 0.0 | |
| | Moved to light | 040902(5)/50% ± 6.1 | | |
| Malt Extract | Dark | 040906(4)/20% ± 2.2 | | |
| | Moved to light | 040902(5)/20% ± 2.8 | 040906(4)/20% ± 2.0 | 040901(3)/10% ± 0.0 |
| Potato Dextrose | Dark | 041004(5)/50% ± 6.1 | | |
| | Moved to light | 040901(3)/70% ± 4.3 | 041004(5)/20% ± 3.2 | |
| Sabouraud | Dark | 041004(5)/20% ± 0.0 | 040906(4)/20% ± 3.2 | 040207(3)/10% ± 0.0 |
| | Moved to light | 040902(5)/60% ± 6.3 | 040906(4)/30% ± 3.9 | 041004(5)/10% ± 2.8 |

TABLE 7

Presence and number of emergent endophytes from ten root cultures of the barley variety 'Propino' inoculated with one of ten endophytes on one of five media for seedlings cultured at 25° C. in the dark for 21 days (n = 15).

| | Growth Medium | | | | | |
|---|---|---|---|---|---|---|
| Isolate | Corn Meal | Czapek Dox | Malt Extract | Potato dextrose | Sabouraud | Totals |
| 040207(3) | 3 | 3 | 2 | 2 | 5 | 15 |
| 040406(3) | 0 | 0 | 0 | 0 | 1 | 1 |
| 040605(2) | 0 | 4 | 2 | 2 | 4 | 12 |
| 040901(3) | 5 | 6 | 2 | 4 | 7 | 24 |
| 040902(5) | 2 | 3 | 3 | 4 | 3 | 15 |
| 040906(4) | 1 | 1 | 0 | 0 | 4 | 6 |
| 040909(3) | 0 | 0 | 0 | 0 | 1 | 1 |
| 041004(5) | 0 | 0 | 0 | 0 | 2 | 2 |
| 041008(5) | 2 | 5 | 3 | 2 | 5 | 17 |
| 041010(3) | 0 | 0 | 1 | 0 | 0 | 1 |
| Totals | 13 | 22 | 13 | 14 | 32 | 94 | plant defences, such as systemic acquired resistance (SAR). The endophyte isolate with the greatest suppression of seed-borne infections also appeared to stop the growth of the serious barley pathogen 'take-all' disease, which is normally transmitted through the soil. This result indicates that some endophytes may have great potential as broad spectrum biocontrol agents.

When the harvest measurements were compared, it was found that the plants with the HI nutrient input had the greatest mean values for all parameters but dry root weight (Table 8). The greatest difference was shown in the dry shoot weight, where the HI nutrient input plants were a mean of 53% greater than the LO (single factor ANOVA, $F_{1,20}$=67.6, $p<0.01$). The mean dry grain weight for the HI treatments was 35% greater than the LO (single factor ANOVA, $F_{1,20}$=56.1, $p<0.01$). Compared with the control, all of the endophyte-inoculated plants had a greater mean number grains per plant for both HI and LO treatments. Overall, the LO treatment produced the greatest number of significant differences compared with the control –22 versus 7 for the HI treatments. The parameters that differed most significantly between the endophyte-inoculated plants and the control for both treatments combined were (in order of importance): mean dry grain weight, mean number of grains and mean dry shoot weight. The mean number of mature heads, mean height and mean dry root weight each had only one value significantly greater value than the control.

TABLE 8

Comparison of the harvest parameters from the barley cultivar 'Propino' between plants inoculated with one of ten endophytes and Controls. Figures are mean percentage differences per plant (n = 15).

|  | Number of grains % vs Control | | Dry shoot weight % vs Control | | Grain Yield % vs Control | |
|---|---|---|---|---|---|---|
| Isolate | HI | LO | HI | LO | HI | LO |
| 040207(3) | 97 | 117 | 91 | 118 | 105 | 104 |
| 040406(3) | 97 | 113 | 84 | 127* | 100 | 91 |
| 040605(2) | 101 | 136** | 102 | 143* | 107 | 115 |
| 040901(3) | 124* | 163** | 103 | 170** | 125** | 117** |
| 040902(5) | 108 | 148** | 88 | 134** | 108 | 127** |
| 040906(4) | 116 | 167** | 98 | 139** | 124** | 129** |
| 040909(5) | 124 | 107 | 100 | 111* | 120** | 96 |
| 041004(5) | 119 | 110 | 103 | 98 | 115* | 88 |
| 041008(5) | 106 | 104 | 95 | 102 | 111 | 104 |
| 041010(3) | 125* | 109 | 106 | 100 | 117** | 88 |

TABLE 8-continued

Comparison of the harvest parameters from the barley cultivar 'Propino' between plants inoculated with one of ten endophytes and Controls. Figures are mean percentage differences per plant (n = 15).

|  | Number of grains % vs Control | | Dry shoot weight % vs Control | | Grain Yield % vs Control | |
|---|---|---|---|---|---|---|
| Isolate | HI | LO | HI | LO | HI | LO |
| Means | 112 | 127 | 97 | 124 | 113 | 106 |
| Control | 100 | 100 | 100 | 100 | 100 | 100 |

**indicates a statistically significant difference of $p < 0.01$ (ANOVA),
*indicates $p < 0.05$.

Plants inoculated with six of the endophytes as defined by SEQ ID NOs: 3 to 12 had significantly greater mean dry shoot weight than the control for the LO nutrient treatments (a range of single factor ANOVAs, three at $p<0.01$ and three at $p<0.05$) but none of the HI nutrient treatments inoculated with the endophytes had a greater mean dry shoot weight than the control. Three of the endophyte isolates (040903(3) (having an nrITS of SEQ ID NO: 6), 040906(4) (having an nrITS of SEQ ID NO: 8) and 040902(5) (having an nrITS of SEQ ID NO: 7)) induced both significantly greater dry shoot weight and mean dry grain weight than the control for the LO nutrient treatments, with 040901(3) (having an nrITS of SEQ ID NO: 6) having 70% greater mean dry shoot weight (single factor ANOVA, $F_{1,28}$=12.65, $p<0.01$) and 040906(4) (having an nrITS of SEQ ID NO: 8) having 29% greater mean dry grain weight (single factor ANOVA, $F_{1,28}$=28.71, $p<0.01$). The endophyte isolate 040901(3) (having an nrITS of SEQ ID NO: 6) had the most number of significantly greater parameter values than the control.

The mean dry grain weight was the parameter with the most significantly greater values than the control (three for the LO treatment and five for the HI), and the mean number of mature heads and mean height had the least significantly greater values than the control (1 each for the LO treatment). Only one of the endophyte isolates produced no significant differences for any parameter compared with the control.

There were disease symptoms on all of the mature plants, with symptoms affecting from 30-100% of leaf and stem tissue. There were no visible signs of disease at the seedling stage (see results above) and the symptoms matched those usually seen in plants infected with *Ramularia collo-cygni* (although some of the plants could also have been infected with the spot form of net blotch).

TABLE 9

Mean harvest measurements per plant for the barley cultivar 'Propino' inoculated with one of 10 different fungal root endophytes and grown under 2 nutrient regimes.

| Treatment, Nutrients | No. of mature heads | No. of grains | Height at maturity mm | Dry shoot weight g | Dry root weight g | Dry grain weight g |
|---|---|---|---|---|---|---|
| 040207(3), LO | 1.26 ± 0.1 | 28.40 ± 3.3 | 57.33 ± 3.9 | 1.32 ± 0.13 | 11.15 ± 0.68 | 1.56 ± 0.07 |
| HI | 1.60 ± 0.3 | 35.00 ± 2.3 | 63.00 ± 2.7 | 1.96 ± 0.09 | 9.34 ± 0.32 | 2.08 ± 0.08 |
| 040406(3), LO | 1.66 ± 0.2 | 27.46 ± 1.8 | 61.60 ± 3.6* | 1.42 ± 0.09* | 9.96 ± 0.44 | 1.36 ± 0.04 |
| HI | 1.33 ± 0.3 | 34.73 ± 3.3 | 61.86 ± 3.6 | 1.82 ± 0.07 | 9.69 ± 0.44 | 1.98 ± 0.15 |
| 040605(2), LO | 1.20 ± 0.3 | 33.00 ± 1.8** | 58.80 ± 3.9 | 1.60 ± 0.11* | 9.63 ± 0.47 | 1.72 ± 0.09 |
| HI | 1.60 ± 0.2 | 36.13 ± 3.9 | 63.40 ± 4.4 | 2.20 ± 0.07 | 9.66 ± 0.41 | 2.12 ± 0.15 |
| 040901(3), LO | 1.60 ± 0.2 | 39.60 ± 3.9** | 59.33 ± 4.3 | 1.90 ± 0.21** | 9.29 ± 0.54 | 1.76 ± 0.02** |

TABLE 9-continued

Mean harvest measurements per plant for the barley cultivar 'Propino' inoculated with one of 10 different fungal root endophytes and grown under 2 nutrient regimes.

| Treatment, Nutrients | No. of mature heads | No. of grains | Height at maturity mm | Dry shoot weight g | Dry root weight g | Dry grain weight g |
|---|---|---|---|---|---|---|
| HI | 1.73 ± 0.2 | 44.40 ± 3.2* | 61.73 ± 4.4 | 2.22 ± 0.15 | 9.39 ± 0.63 | 2.49 ± 0.08** |
| 040902(5), LO | 1.33 ± 0.3 | 35.80 ± 2.8** | 58.66 ± 4.0 | 1.50 ± 0.15** | 11.75 ± 0.31* | 1.90 ± 0.07** |
| HI | 1.40 ± 0.2 | 38.93 ± 2.6 | 64.20 ± 4.2 | 1.90 ± 0.07 | 9.28 ± 0.40 | 2.14 ± 0.08 |
| 040906(4), LO | 1.60 ± 0.2 | 40.40 ± 2.0** | 60.06 ± 4.7 | 1.56 ± 0.09** | 10.05 ± 0.27 | 1.94 ± 0.04** |
| HI | 1.80 ± 0.3 | 41.53 ± 3.2 | 63.13 ± 4.6 | 2.12 ± 1.0 | 9.69 ± 0.35 | 2.46 ± 0.07** |
| 040909(5), LO | 1.73 ± 0.2 | 26.00 ± 2.5 | 50.93 ± 3.6 | 1.24 ± 0.02* | 9.40 ± 0.51 | 1.44 ± 0.11 |
| HI | 2.00 ± 0.1 | 44.53 ± 3.3 | 59.27 ± 5.1 | 2.16 ± 0.12 | 9.71 ± 0.31 | 2.38 ± 0.04** |
| 041004(5), LO | 1.40 ± 0.1 | 26.73 ± 2.7 | 51.20 ± 3.2 | 1.1 ± 0.04 | 9.23 ± 0.52 | 1.32 ± 0.09 |
| HI | 1.93 ± 0.2 | 42.73 ± 3.3 | 61.33 ± 4.5 | 2.22 ± 0.09 | 8.63 ± 0.30 | 2.28 ± 0.09* |
| 041008(5), LO | 2.00 ± 0.1* | 25.20 ± 2.3 | 52.46 ± 3.2 | 1.14 ± 0.01 | 8.96 ± 0.32 | 1.56 ± 0.05 |
| HI | 1.73 ± 0.2 | 37.93 ± 2.7 | 59.27 ± 4.4 | 2.06 ± 0.13 | 9.27 ± 0.33 | 2.2 ± 0.07 |
| 041010(3), LO | 1.73 ± 0.2 | 26.40 ± 2.3 | 46.26 ± 4.2 | 1.12 ± 0.02 | 8.47 ± 0.32* | 1.32 ± 0.06 |
| HI | 2.06 ± 0.3 | 45.06 ± 2.4* | 61.93 ± 4.6 | 2.28 ± 0.06 | 9.85 ± 0.39 | 2.32 ± 0.07** |
| Control, LO | 1.60 ± 0.1 | 24.26 ± 2.4 | 51.33 ± 2.6 | 1.12 ± 0.05 | 10.11 ± 0.63 | 1.5 ± 0.07 |
| HI | 1.80 ± 0.2 | 35.93 ± 2.5 | 57.73 ± 4.2 | 2.16 ± 0.2 | 9.58 ± 0.43 | 1.99 ± 0.08 |
| Mean, LO | 1.56 | 30.3 | 55.2 | 1.37 | 9.82 | 1.58 |
| HI | 1.73 | 39.7 | 61.5 | 2.1 | 9.46 | 2.13 |

*indicates a statistically significant difference between treatment and control of $p < 0.05$ (ANOVA),
**indicates $p < 0.01$ (n = 15).

All of the root pieces from the endophyte-inoculated plants produced growth from root endophytes at the end of the experiment, which matched the morphology of the original inoculants.

When a test for the vertical transmission potential of the endophytes was performed, it was found that only one root piece (3%) produced the emergent endophyte 040901(3) (having an nrITS of SEQ ID NO: 6). For the horizontal transmission test, three root pieces (10%) produced emergents of 040901(3) (having an nrITS of SEQ ID NO:6). The endophyte isolate 040906(4) (having an nrITS of SEQ ID NO: 8) did not emerge from any root pieces.

It has been shown that inoculation with fungal root endophytes derived from Hordeum murinum subsp. murinum L. significantly increased grain yield, dry shoot weight and number of grains per plant in the barley cultivar 'Propino' grown in nutrient-starved conditions. Further, the increases in these parameters were greatest with the lowest nutrient regime. Nearly all of the ten endophyte isolates produced some improvement in at least one barley trait, with only one producing no measurable benefit. The most important result from a growers' point of view was that the endophytes induced a greater improvement in mean dry grain weight than any other yield parameter.

Three of the endophyte isolates selected from SEQ ID NOs: 3 to 12 performed significantly better than the others, and these were isolated from wall barley growing on the same site. When combined, the three endophytes produced a mean increase of 59% in the number of grains, a 48% increase in dry shoot weight and a 24% increase in grain dry weight for the LO nutrient input. The greater improvement in these traits associated with the lowest nutrient input contrasts with the findings of Murphy et al. (2014) who found that an increase in dry grain weight induced by the model endophyte Piriformospora indica was only apparent with a higher nutrient input. The isolated endophytes presented herein give more significant improvements in important barley traits in the more nutrient-stressed plants.

TABLE 10

FRE isolate performances on the barley cultivar 'Propino'. Figures are means per plant (n = 15).

| | | | HI nutrient treatment | | | HI nutrients | LO nutrients | |
| --- | --- | --- | --- | --- | --- | --- | --- | --- |
| Isolate | Nearest BLAST match | % Identical | Dry grain weight g | Dry shoot weight g | Dry root weight g | Grain Yield vs Control % | Grain Yield vs Control % | Seed-borne control % |
| 040207(3) | Paecilomyces marquandii JQ013003[1] | 98.6 | 2.08 ± 0.08 | 1.96 ± 0.09 | 9.34 ± 0.32 | 105 | 104 | 20 |
| 040406(3) | Viridispora alata JF832678[2] | 94 | 1.98 ± 0.15 | 1.82 ± 0.07 | 9.96 ± 0.44 | 100 | 91 | 50 |
| 040605(2) | Cladosporium sp. GQ169491[3] | 99.6 | 2.12 ± 0.15 | 2.2 ± 0.08 | 9.66 ± 0.41 | 107 | 115 | 50 |

TABLE 10-continued

FRE isolate performances on the barley cultivar 'Propino'. Figures are means per plant (n = 15).

| Isolate | Nearest BLAST match | % Identical | HI nutrient treatment | | | HI nutrients | LO nutrients | Seed-borne control % |
| | | | Dry grain weight g | Dry shoot weight g | Dry root weight g | Grain Yield vs Control % | Grain Yield vs Control % | |
|---|---|---|---|---|---|---|---|---|
| 040901(3) | *Penicillium brevicompactum* EU587331[1] | 94.8 | 2.49 ± 0.08 | 2.22 ± 0.15 | 9.39 ± 0.63 | 125** | 117** | 100 |
| 040902(5) | *Pyrenochaeta unguis-hominis* JX966641[4] | 98 | 2.14 ± 0.08 | 1.9 ± 0.07 | 9.28 ± 0.40 | 108 | 127** | 60 |
| 040906(4) | Uncultured *Metarhizium* KC797571[2] | 95.5 | 2.46 ± 0.07 | 2.12 ± 1 | 9.69 ± 0.35 | 124** | 129** | 30 |
| 040909(5) | Uncultured fungus FJ820798 (*Penicillium*?) | 93.8 | 2.38 ± 0.04 | 2.16 ± 0.12 | 9.71 ± 0.31 | 120** | 96 | 70 |
| 041004(5) | *Exophiala oligosperma* JN655630[5] | 100 | 2.28 ± 0.08 | 2.22 ± 0.08 | 8.63 ± 0.30 | 115* | 88 | 20 |
| 041008(5) | *Penicillium brevicompactum* FJ884117[1] | 99.6 | 2.2 ± 0.07 | 2.06 ± 0.13 | 9.27 ± 0.33 | 111 | 104 | 100 |
| 041010(3) | *Penicillium* sp. FR822844[1] | 99.4 | 2.32 ± 0.07 | 2.28 ± 0.06 | 9.85 ± 0.39 | 117** | 88 | 20 |
| Means | n/a | n/a | 2.25 | 2.09 | 9.48 | 113 | 106 | 52 |
| Control | n/a | n/a | 1.99 ± 0.08 | 2.16 ± 0.2 | 9.58 ± 0.43 | n/a | n/a | 0 |

**indicates $p < 0.01$,
*indicates $p < 0.05$
Fungal orders (superscript numbers on Nearest BLAST match):
[1] = Eurotiales,
[2] = Hypocreales,
[3] = Capnodiales,
[4] = Pleosporales,
[5] = Chaetothyriales These results suggest that crop inoculants using selected endophytes would have the most beneficial impacts on very low nutrient sites, allowing growers to reduce fertiliser inputs while still maintaining acceptable yields. The reduction in economic and environmental costs could potentially be great, particularly for subsistence farmers in poorer parts of the world. Some barley traits (for instance, kernel weight) are more genetically determined and thus more stable as compared to other traits (such as seed number). Growers are more interested in crop yield per area, whereas in a controlled environment study such as presented here, one can more easily measure results per plant or pot. When translated to the number of plants per square metre, then the planting density used in the experiments here was representative of that usually recommended, thus enabling interpretive translation to field conditions.

Effect on Important Agronomic Traits for Drought-Stressed Barley

The five fungal root endophytes isolated from wild populations of Hmm, as described above for SEQ ID NOs: 6, 8, 13, 14 and 15, were prepared from single spores, following Murphy et al. (2014).

Untreated seeds of the *H. vulgare* cultivar Propino (Goldcrop Seeds, Cork, Ireland) were used. Seeds were surface-sterilised by soaking in 5% NaClO for 15 min, rinsing three times with 70% ethanol and then rinsing five times with pure water. The growth compost of John Innes No. 3 formulation (Westland Horticulture Limited) was sterilised by autoclaving and placed into 1.5 litre washed and sterilised plastic pots (soaked for 2 hours in 5% NaClO then rinsed×5 with tap water). For each inoculation treatment (including a control), twenty five seeds of barley, in 5 pots containing 5 seeds each, were sown at 30 mm depth and inoculated with one of the five endophytes. The inoculant solution was prepared by mixing 10 mg of each fungal culture with 5 ml of sterile ultra-pure water and stirring with a magnetic bar for 2 hr at 35° C. 250 µl of the solution was directly inoculated onto each seed. For the controls, the seeds were inoculated with 250 µl of pure water.

Pots were placed into two controlled environment chambers, then randomly relabelled with a single number by a third party, to produce a double-blind and randomised setup. The pots were moved to a new position in blocks of 5 pots every 3 days. The environmental settings of the growth cabinet (Conviron PGR14) were programmed to produce a 14 hr photoperiod at a compost surface illumination of 220 µmol·m$^{-2}$ s$^{-1}$, a photoperiod temperature of 23° C. reducing to 12° C. in the dark period and a constant 70% relative humidity.

Three covered culture dishes containing five sterilised barley seeds on malt extract agar (Fluka 38954) were kept in the growth chamber during the experimental period to test for seed surface sterilisation success and to monitor any contamination that may be present from seed-produced fungal infection.

The seedlings were thinned to three plants per pot twelve days after germination, when the Germination Index (GI) was calculated using the formula:

$$GI = ((G_t/G_n)/G_n) \qquad (1)$$

where $G_t$=cumulative number of days to germination for all seeds and $G_n$=total number of seeds germinated. Soil moisture was measured daily using a Delta-T Devices HH2 WET sensor kit (Delta-T Devices, Cambridge, UK) and soil moisture content at a depth of 50 mm was maintained at 45%±10% (representing field capacity) from germination until 14 days after germination by watering with tap water. After this period, half of the plants were given lower water inputs (drought stressed; DS) and half were given higher (non-droughted, ND) water input. For the ND treatments, the soil moisture content was maintained at approximately 45% as before; for DS treatments, pots were only watered when the soil moisture content was between 10% and 15% and the plants showed visible signs of stress (colour change, wilting), when the pots were watered until soil moisture content was again at field capacity (~45%). Total water input for the ND treatment was 6.39 litre per pot compared to 3.47 for the DS treatment. All pots were given a liquid fertiliser (Bayer Phostrogen®) at each watering of the DS treatment (total nutrient input per plant was: ammoniacal N=0.02 g, ureic N=0.12 g, Total N=0.14 g, P=0.09 g, K=0.22 g, Mg=0.02 g, S=0.04 g, Ca=0.02 g and traces of Boron, Copper, Iron, Manganese, Molybdenum and Zinc). A liquid fertiliser was used because the variable water input would be biased by incomplete nutrient delivery in the DS treatment if a solid fertiliser formulation were used.

The number of days to reach selected Zadoks stages (Zadoks et al. 1974) was recorded for each plant. Plants were grown for 92 days (13 weeks) from date of sowing, then harvested and processed over a period of two days. Before processing the plants, four 5 mm pieces of mid-section root from each plant were surface-sterilised and incubated on half-strength malt extract agar at 25° C. in the dark to test for endophyte presence. Endophyte emergence was recorded over the next 35 days, and emergents were identified by morphological examination and by sequencing of the internal transcribed region (ITS) of nuclear ribosomal DNA (nrDNA). For the DNA analysis, 20 mg of fungal material was scraped from the agar surface and placed into shaker tubes. DNA was extracted using a Qiagen DNeasy mini kit, following the Qiagen protocol, producing 200 μl of DNA extract for each isolate. PCR was carried out on the DNA extracts using the nuclear ribosomal DNA (rDNA) internal transcribed spacer (ITS) primers ITS1 (forward primer) (SEQ ID NO: 1-5' TCCGTAGGTGAACCTGCGG 3') and ITS4 (reverse primer) (SEQ ID NO: 2-5' TCCTCCGCTTATTGATATGC 3'). The thermal cycling parameters were programmed to optimise primer annealing, consisting of: 3 min at 95° C.; 9 cycles of 1 min at 94° C., 1 min at 56° C., 2 min at 72° C.; 20 cycles of 30 sec at 94° C., 1 min at 56° C., 3 min at 72° C.; a final extension for 7 min at 72° C. PCR products were cleaned up using Exonuclease (New England Biolabs) and Shrimp Alkaline Phosphatase (ExoSAP; Roche). Purified PCR products underwent cycle sequencing using the reverse ITS4 primer (4 pmol; SEQ ID NO: 2) or forward ITS1 primer (4 pmol; SEQ ID NO: 1) in separate reactions with the ABI BigDye 3.1 kit (Foster City, Calif.). The products were further purified using a BigDye XTerminator purification kit and protocol. DNA was sequenced using an Applied Biosystems 3130xL Genetic Analyzer. The recovered sequences from the roots of each treatment were compared to the sequences of the original inoculants.

Pots were selected for processing in random order. Measurements were made for fresh and dry weights of grains, shoots and roots; mean height of tillers to tip of highest awn; number of heads; number of tillers and number of grains per head. All plant parts were separately dried in ovens for 7 days at 65 C before dry weights were measured. Treatment identity was only revealed after all measurements had been made. Data analysis was carried out using single and two-factor ANOVA with Bonferroni correction and Pearson's correlation statistical analyses supplied with the Data Analysis module within Microsoft Excel©.

Results

Germination index was not significantly influenced by four different endophyte strains but one of the endophyte treatments, 040901(3), produced a significantly greater GI than the control (single factor ANOVA, $F_{1,58}$=5.06, P<0.05). For both the non-droughted (ND) and drought-stressed (DS) treatments all of the endophyte treatments induced between 9 and 13 days earlier flowering than the control (ANOVA, $F_{5,84}$=22.37, P<0.001 and ANOVA, $F_{5,84}$=78.34, P<0.001 respectively). The mean number of days to reach flowering was 75 for ND plants and 83 for the DS plants. However, only 2.2% of the DS plants had reached full maturity at the time of harvest compared to 43% for the ND plants. When the harvest data was compared, it was found that the ND plants had significantly greater values (P<0.05) than the DS plants for all measured traits except root weight (FIG. 1). In particular, the number of grains and dry grain weight was nearly 4 times greater, and the number of tillers and dry shoot weight were 1.5 times greater. In contrast, the DS plants had a mean dry root weight per plant that was nearly three times greater than the ND plants. For the ND plants, the number of mature shoots per plant was 1.7 times greater than the DS plants (single factor ANOVA, $F_{1,58}$=78.18, P<0.001). The ND plants showed no signs of diseased above-ground tissue, in contrast to the DS plants where 70% of all plants had some proportion of the above-ground tissue displaying symptoms of net blotch disease (*Pyrenophora teres* f. *teres*). Further analysis revealed a significant difference between treatments (single factor ANOVA, $F_{5,84}$=16.39, P<0.001), where all of the endophyte treated plants had less disease symptoms than the controls (P<0.001).

Figure 2:
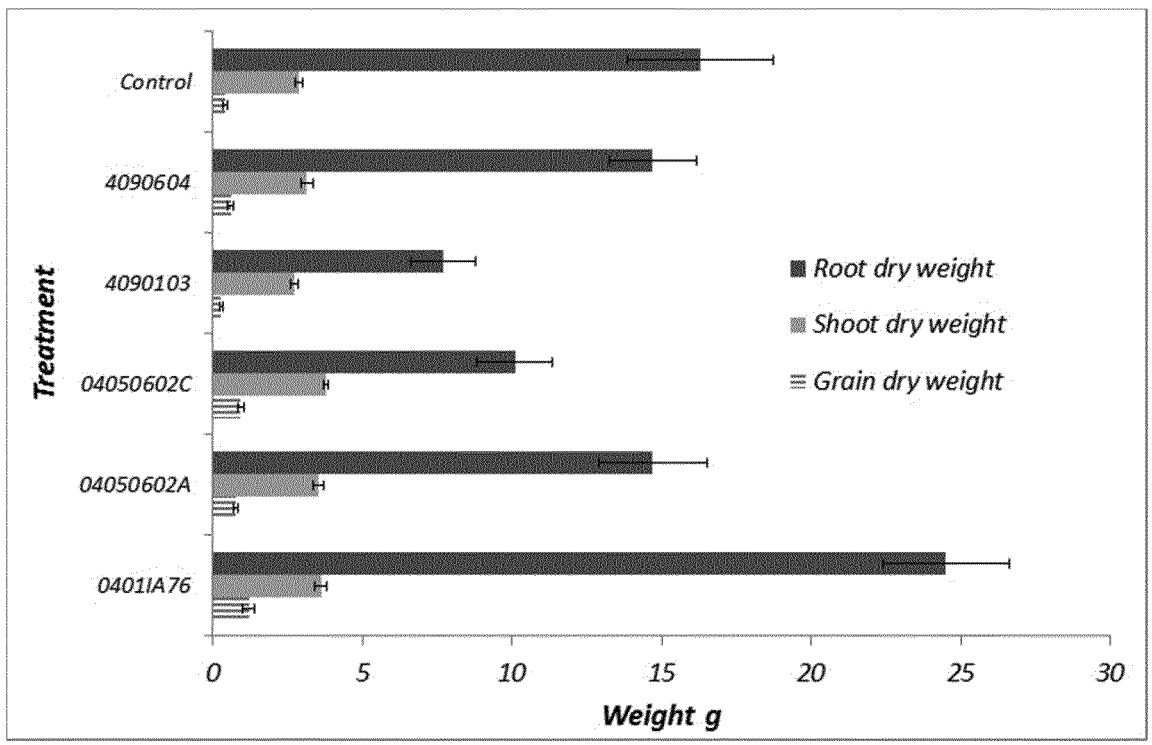
FIG. 2 is a graph illustrating dry root, shoot and grain weights±S.E. for a drought-stressed (DS) barley cultivar for endopyhte and control treatments.
Figure 3:
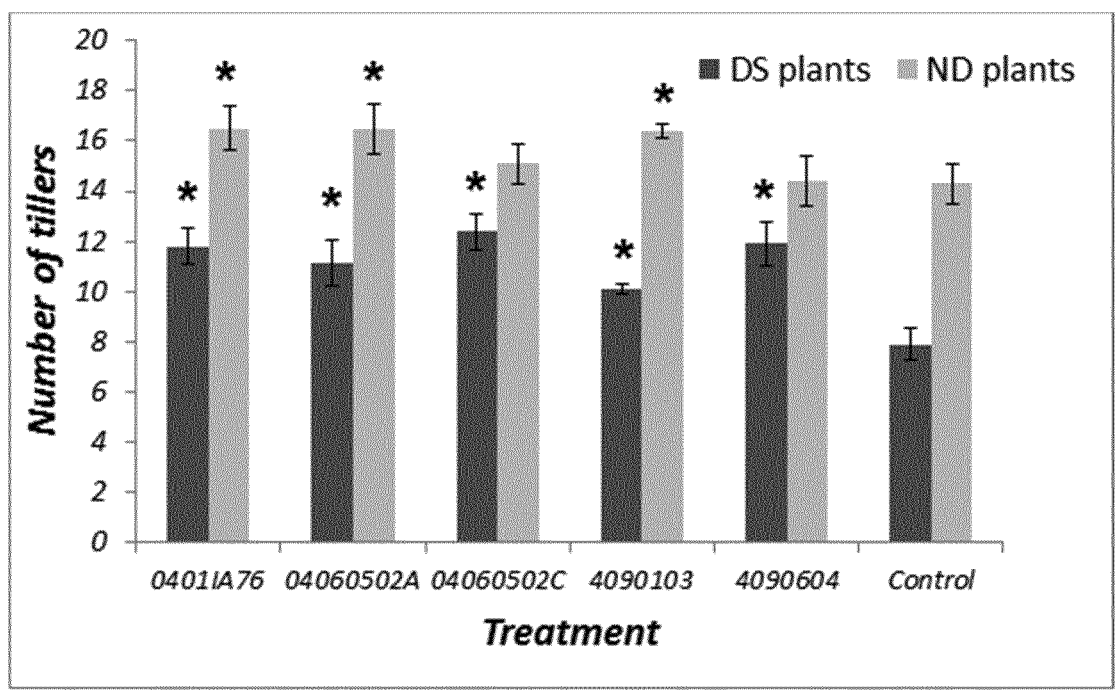
FIG. 3 is a graph illustrating the number of tillers±S.E. per plant for a non-drought stressed (ND) and drought-stressed (DS) barley cultivar for endopyhte and control treatments. Significant differences (P<0.05) between endophyte and control treatments are indicated with *.

A significant interaction was found between fungal strain and water treatment for several traits: number of tillers per plant (P<0.05), height (P<0.001), shoot dry weight (P<0.05), number of grains (P<0.05) and root dry weight (P<0.001). While there were significant differences between endophyte treatments and controls for both ND and DS plants—where the endophyte treated plants generally out-performed the controls—the increases in desirable barley traits due to endophyte inoculation were greater for the DS plants. Here, compared to the control, an improvement was found in barley traits for all endophyte treatments except for mean number of grains and mean dry root weight (Table 11). The mean root dry weight for all endophyte-inoculated plants was actually greater, with one exception, in the control plants for both DS and ND treatments (single factor ANOVA, $F_{5,84}$=12.56, P<0.05 and $F_{5,84}$=16.39, P<0.001 respectively), indicating preferential allocation of resources to above-ground parts in the endophyte treatments. Results were not consistent across all endophyte treatments, with some endophytes performing much better than others (FIG. 2). In particular, the endophyte 0401IA76 (having an nrITS of SEQ ID NO: 15) induced significant increases (P<0.01) for all traits, even root dry weight (P<0.05). For the DS plants only two endophyte treatments (040901(3) (having an nrITS of SEQ ID NO: 6) and 040906(4) (having an nrITS of SEQ ID NO: 8)) had no measurable increases in dry grain and shoot weight compared to the controls. The trait that showed the greatest significant difference in the DS plants was in mean number of tillers (single factor ANOVA, $F_{5,84}=5.26$, P<0.001), where all of the endophyte treatments induced a greater number of tillers per plant (FIG. 3). Here there was a significant correlation between mean number of tillers and both mean shoot dry weight (Pearson's r=0.85, P<0.001) and mean grain dry weight (Pearson's r=0.57, P<0.01).

Final overall comparisons between control and endophyte inoculated plants revealed a significant overall improvement over the control in desirable barley traits for the DS plants (P<0.05) but with no detectable difference for the ND plants. At the end of the experiment, the three covered culture dishes containing five sterilised barley seeds on malt extract agar (Fluka 38954) that were kept in the growth chamber during the experimental period produced no evidence of seed-produced fungal infection.

inoculation treatments (including a control), twenty five seeds of barley, in 5 pots containing 5 seeds each, were sown at 30 mm depth and either inoculated with an inoculant solution of 250 µl containing one of the five endophytes or a an inoculant solution of 250 µl containing a combination of all five endophytes (AllEndos). The inoculant solution was prepared by mixing 10 mg of each fungal culture with 8 ml of pure water and stirring with a magnetic bar for 2 mins at 25° C. 250 µl of the solution was directly inoculated onto each seed. For the controls, the seeds were inoculated with 250 µl pure water. Every seed was also directly inoculated with a 250 µl solution of the common and serious barley pathogen *Gaeumannomyces graminis* var. *tritici* ("take-all") (GenBank Accession KF018415), prepared as above.

TABLE 11

Trait values for endophyte inoculated barley plants, showing significant negative (−−) and positive (++) differences in barley traits between endophyte-inoculated and control plants for non drought-stressed (ND) and drought-stressed (DS) plants.

| Trait | ND/DS | 0401IA76 | 040605(2A) | 040605(2C) | 040901(3) | 040906(4) | Control |
|---|---|---|---|---|---|---|---|
| Proportion of diseased tissue | ND | 0%/0 | 0%/0 | 0%/0 | 0%/0 | 0%/0 | 0% |
|  | DS | 12%/++,** | 12%/++,** | 16%/++,** | 16%/++,** | 16%/++,** | 44% |
| Mean height, cm | ND | 78.2/0 | 83.0/++,** | 81.6/++,** | 87.4/++,** | 87.8/++,** | 74.6 |
|  | DS | 66.2/++,** | 63.8/0 | 65.8/++,* | 63.2/0 | 66.2/++,** | 62.8 |
| Mean dry grain weight, g | ND | 1.86/++,** | 1.65/++,** | 1.72/++,** | 1.26/0 | 1.36/0 | 1.27 |
|  | DS | 1.20/++,** | 0.76/++,** | 0.92/++,** | 0.26/0 | 0.59/0 | 0.39 |
| Mean dry shoot weight, g | ND | 5.68/++,** | 4.65/0 | 4.77/0 | 4.09/−−,** | 4.62/0 | 4.87 |
|  | DS | 3.60/++,** | 3.53/++,** | 3.78/++,** | 2.72/0 | 3.13/0 | 2.86 |
| Mean number of grains | ND | 128/++,** | 129/++,** | 111/++,** | 99/0 | 89/0 | 86 |
|  | DS | 47/++,* | 22/0 | 47/++,* | 15/0 | 24/0 | 21 |
| Mean number of tillers | ND | 50/++,* | 50/++,* | 45/0 | 49/++,* | 44/0 | 43 |
|  | DS | 12/++,** | 11/++,** | 12/++,** | 10/++,* | 12/++,** | 8 |
| Mean dry root weight | ND | 3.0/−−,* | 1.1/−−,* | 1.9/−−,* | 6.3/−−,* | 7.1/0 | 11.4 |
|  | DS | 24.5/++,* | 14.7/−−,** | 10.1/−−,** | 7.7/−−,** | 14.7/0 | 16.3 |

Data are for means per plant;
0 indicates no difference,
*indicates p < 0.05,
**indicates p < 0.01.

Effect on Important Agronomic Traits for Multiply-Stressed Barley

The five fungal root endophytes isolated from wild populations of Hmm, as described above for SEQ ID NOs: 6, 8, 13, 14 and 15, were prepared from single spores, following Murphy et al. (2014).

Untreated seeds of the barley cultivar 'Propino' (Goldcrop Seeds, Cork, Ireland) were used. Seeds were surface-sterilised by soaking in 5% NaClO for 15 min, rinsing three times with 70% ethanol and then rinsing five times with pure water. The growth compost of John Innes No. 3 formulation (Westland Horticulture Limited) was placed into 1.5 litre washed and sterilised (soaked for 2 hours in 5% NaClO then rinsed×5 with tap water) plastic pots. For each of the seven Pots were placed into a controlled environment chamber, then randomly relabelled with a single number by a third party, to produce a double-blind and randomised setup. The pots were moved to a new position within the growth chamber every 3 days. The environmental settings of the growth cabinet (Conviron PGR14) were programmed to produce a 14 hr photoperiod at a compost surface illumination of 220 µmol·m$^{-2}$ s$^{-1}$, a photoperiod temperature of 33° C. reducing to 12° C. in the dark period and a photoperiod relative humidity of 45%, increasing to 65% in the dark.

Three covered culture dishes containing five sterilised barley seeds on malt extract agar (Fluka 38954) were kept in the growth chamber during the experimental period to test for seed surface sterilisation success and to monitor any contamination that may be present from seed-produced fungal infection.

The seedlings were thinned to three plants per pot, 12 days after germination, producing 15 individual plant replicates for each treatment. A Germination Index (GI) was calculated using the formula:

$$GI = ((G_t/G_n)/G_n) \quad (2)$$

where $G_t$ is the cumulative number of days to germination for all seeds and $G_n$ the total number of seeds germinated. Soil moisture content at a depth of 50 mm was measured daily using a Delta-T Devices HH2 WET sensor kit (Delta-T Devices, Cambridge, UK) and pots were watered with tap water only when the soil moisture content was between 10% and 15% which was when the barley plants were starting to wilt and showed a drought-associated colour change. The pots were watered until soil moisture content was at field capacity (~45%). Total water input was 4.19 litres per pot. All pots were given a liquid fertiliser (Bayer Phostrogen®) at each watering. Total nutrient input per plant was: ammoniacal N=4 mg, ureic N=20 mg, Total N=24 mg, P=20 mg, K=40 mg, Mg=4 mg, S=8 mg, Ca=4 mg and traces of Boron, Copper, Iron, Manganese, Molybdenum and Zinc. Inputs for nitrogen (N), phosphorous (P) and potassium (K) were approximately 6%, 17% and 16% respectively of that recommended for spring barley growing on low-nutrient soils (teagasc.ie/crops/winter/fertilisers/winter_cereals_fertiliser-requirements.pdf), so plants were severely nutrient-stressed. A liquid fertiliser was used because the low water input may have resulted in incomplete nutrient delivery if a solid fertiliser formulation were used.

A further set of 25 plants for each treatment were grown in close to optimal conditions (OC), with the environmental settings programmed to produce a 14 hr photoperiod at a temperature of 21° C. reducing to 12° C. in the dark period and a constant 70% relative humidity. The seedlings were thinned to three plants per pot, 12 days after germination, producing 15 individual plant replicates for each treatment. A Germination Index (GI) was calculated as above. Plants were watered to maintain the compost at near field capacity and total water input was 6.39 litres per pot. Nutrient input per plant was approximately five times that of the stressed plants (ammoniacal N=20 mg, ureic N=100 mg, Total N=120 mg, P=90 mg, K=220 mg, Mg=20 mg, S=40 mg, Ca=20 mg and traces of Boron, Copper, Iron, Manganese, Molybdenum and Zinc). Again, the pots were moved to a new position within the growth chamber every 3 days.

The number of days to reach selected Zadoks stages (Zadoks et al. 1974) was recorded for each plant. Plants were grown for 90 days (13 weeks) from date of sowing, then harvested and processed in one day. Before processing the plants, four 5 mm pieces of mid-section root from each plant were surface-sterilised and incubated on half-strength malt extract agar at 25° C. in the dark to test for endophyte presence. Endophyte emergence was recorded over the next 35 days, and emergents were identified by morphological examination and by sequencing of the internal transcribed region (ITS) of nuclear ribosomal DNA (nrDNA). For the DNA analysis, 20 mg of fungal material was scraped from the agar surface and placed into shaker tubes. DNA was extracted using a Qiagen DNeasy mini kit, following the Qiagen protocol, producing 200 μl of DNA extract for each isolate. PCR was carried out on the DNA extracts using the nuclear ribosomal DNA (rDNA) internal transcribed spacer (ITS) primers ITS1 (forward primer) (SEQ ID NO: 1-5' TCCGTAGGTGAACCTGCGG 3') and ITS4 (reverse primer) (SEQ ID NO: 2-5' TCCTCCGCTTATTGATATGC 3'). The thermal cycling parameters were programmed to optimise primer annealing, consisting of: 3 min at 95° C.; 9 cycles of 1 min at 94° C., 1 min at 56° C., 2 min at 72° C.; 20 cycles of 30 sec at 94° C., 1 min at 56° C., 3 min at 72° C.; a final extension for 7 min at 72° C. PCR products were cleaned up using Exonuclease (New England Biolabs) and Shrimp Alkaline Phosphatase (ExoSAP; Roche). Purified PCR products underwent cycle sequencing using the reverse ITS4 primer (4 pmol; SEQ ID NO: 2) or forward ITS1 primer (4 pmol; SEQ ID NO: 1) in separate reactions with the ABI BigDye 3.1 kit (Foster City, Calif.). The products were further purified using a BigDye XTerminator purification kit and protocol. DNA was sequenced using an Applied Biosystems 3130xL Genetic Analyzer. The recovered sequences from the roots of each treatment were compared to the sequences of the original inoculants.

Pots were selected for processing in random order. Measurements were made for each plant of fresh and dry weights of shoots and roots, mean height of plants to tip of highest leaf and number of tillers. Shoot and root tissue from each plant of the MS treatment was inspected for signs of *Gaeumannomyces graminis* var. *tritici* infection and the degree of infection estimated as a proportion of total tissue showing signs of disease. All plant parts were separately dried in ovens for 7 days at 65° C. before dry weights were measured.

Data analysis was carried out using single and two-factor ANOVA with Bonferroni correction and Pearson's correlation statistical analyses supplied with Datadesk® 6.1.

Results

Figure 4:
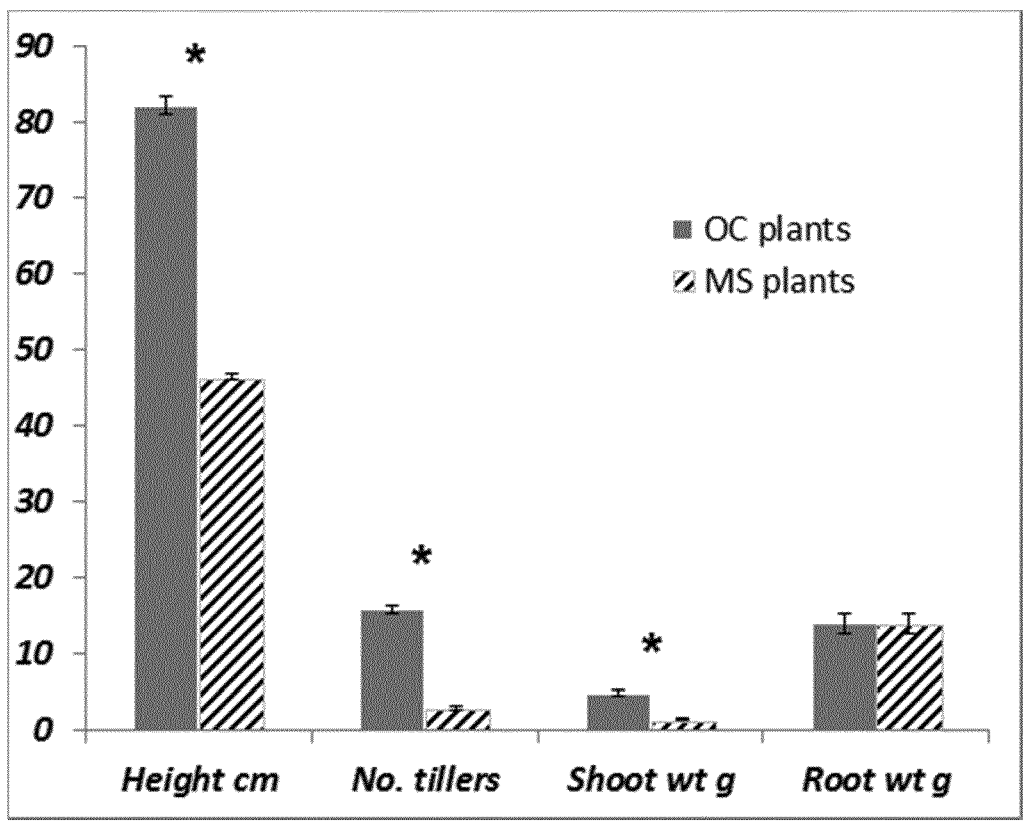
FIG. 4 is a graph illustrating the mean harvest values for selected barley traits between barley grown under optimal conditions (OC) and under multiple stresses (MS). Items marked with '*' indicate significantly greater values for OC treatment (P<0.01).

While two of the multiply-stressed (MS) endophyte treatments, 040605(2A) (having an nrITS of SEQ ID NO: 13) and 040605(2C) (having an nrITS of SEQ ID NO: 14), had a greater germination index (GI) than the control (P<0.01), there was no overall difference in germination index between endophyte treatments and control. Large and significant differences were found between optimally grown plants (OC) and plants subjected to multiple stresses (MS) (Table 12). The main difference was that all of the OC control and treatment plants survived until the end of the experiment, whereas only 13% of MS control plants survived. However, over 80% of the endophyte-inoculated MS plants survived. For two of the MS endophyte treatments, 040906(4) (having an nrITS of SEQ ID NO: 8) and 040605 (2A) (having an nrITS of SEQ ID NO: 13), all of the plants survived. Although all of the OC plants produced seeds, only 10% of MS plants produced stems with rudimentary flowering structures, and none of these produced any heads with grains. Most measured barley traits showed greater values for the OC plants (FIG. 4); the mean height of OC plants was twice that of the MS plants; the mean number of tillers for the OC plants was five times greater than the MS and the mean shoot dry weight for the OC plants was over three times greater than the MS. However, the mean root dry weight was exactly the same for both OC and MS plants. The root dry weight for the control plants was greater than all endophyte-inoculated plants in the OC treatment, whereas in the MS plants the root dry weight for all endophyte-inoculated plants was greater than the control. Final overall comparisons between control and endophyte inoculated plants revealed a significant overall improvement over the control in agronomic barley traits for the MS plants (P<0.01) but with no detectable differences for the OC plants.

Figure 5:
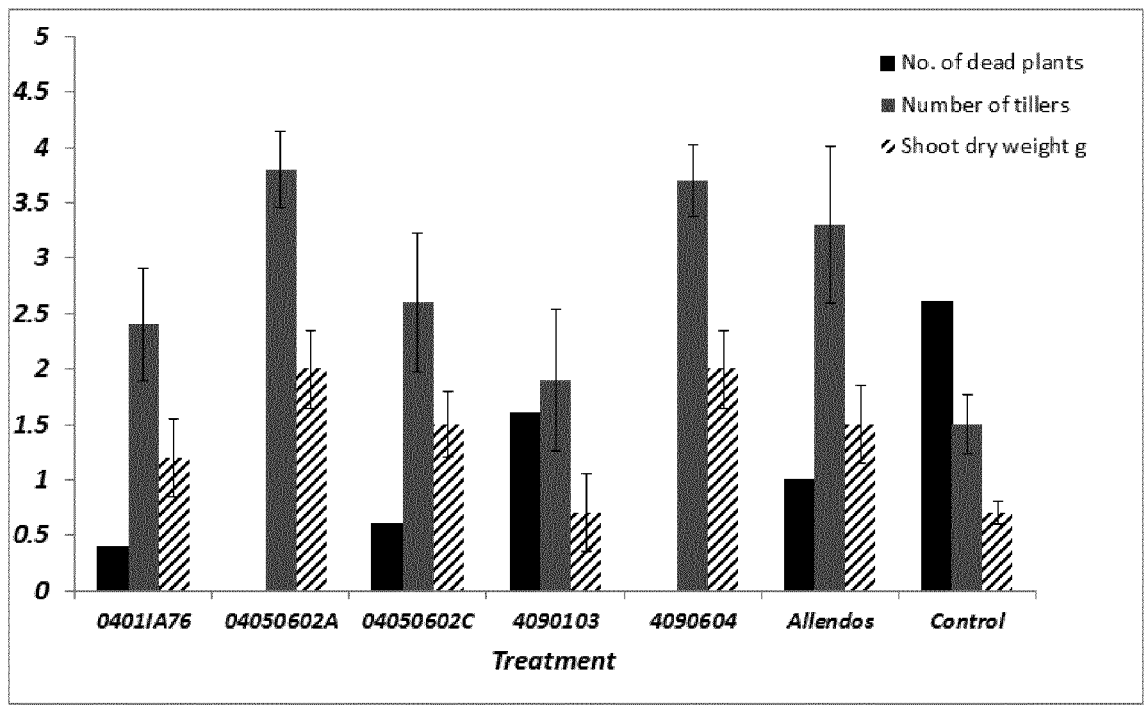
FIG. 5 is a graph illustrating the number of dead plants per pot of 3 plants, number of tillers per plant±S.E. and shoot dry weight per plant±S.E. for barley grown under multiple stresses (MS).
Figure 6:
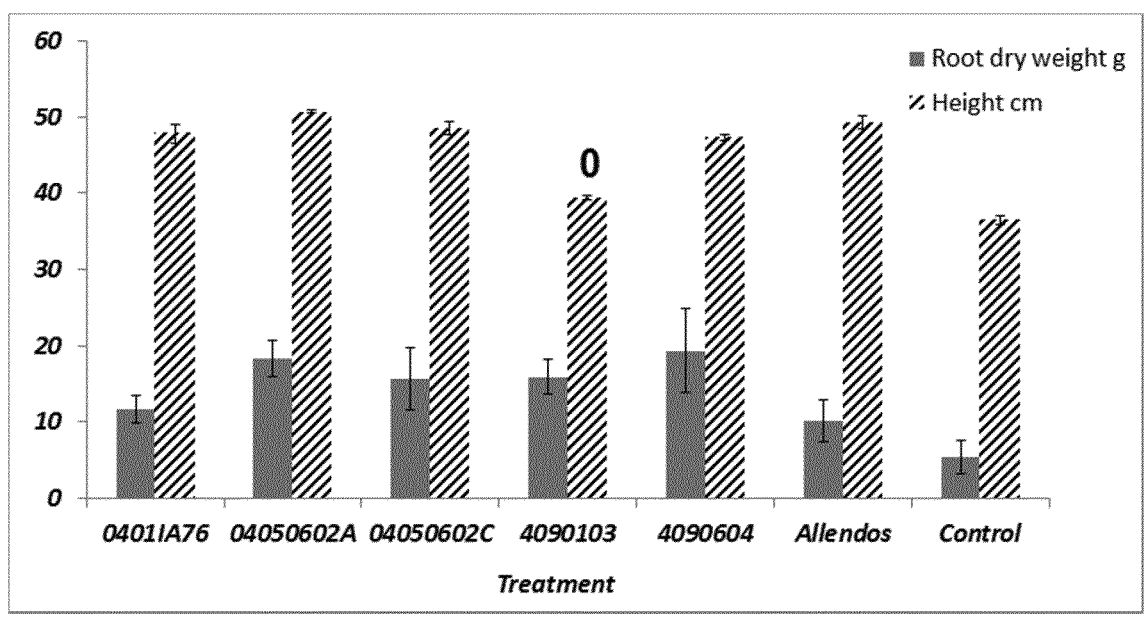
FIG. 6 is a graph illustrating the mean root dry weight±S.E. and mean plant height±S.E. for barley grown under multiple stresses (MS). All values for endophyte treatments, except those marked with '0', are significantly greater (P<0.05) than the control.

For the MS plants that survived until the end of the experiment, we found significant differences in trait performance between control and endophyte-inoculated plants (FIG. 5 and FIG. 6). The mean root dry weight differed significantly between treatments (single factor ANOVA, $F_{6,98}$=8.32, P<0.001), where all of the endophyte treatments had greater root dry weight than the control (P<0.001). The mean plant height, shoot dry weight and number of tillers for the endophyte treatments were all significantly greater than the control (P<0.05), with one exception: there was no detectable difference in shoot dry weight and number of tillers between the control and the endophyte treatment 040901(3) (having an nrITS of SEQ ID NO: 6). The combined endophyte inoculant (AllEndos) was the treatment that gave the greatest improvement for all harvest traits (number of dead plants, plant height, number of tillers, shoot dry weight, root dry weight) in the multiply-stressed plants (P<0.01 for every trait).

No difference was found between treatments in the MS plants for the proportion of root and shoot tissue displaying signs of Gaeumannomyces graminis var. tritici infection, where all plants had less than 5% of total root tissue with disease symptoms, but with no visible symptoms on above ground tissue.

At the end of the experiment, the three covered culture dishes containing five sterilised barley seeds on malt extract agar (Fluka 38954) that were kept in the growth chamber during the experimental period produced no evidence of seed-produced fungal infection.

A mean 50% (182) of root pieces that were removed from the MS plants at harvest produced fungal endophyte emergents. When we compared the emergent endophyte ITS sequences with the original inoculants, it was found that each of the recovered sequences exactly matched that of the original.

This final study combines the stresses that were tested separately in the previous detailed experiments (i.e. nutrient, drought, pathogen) and clearly illustrates the benefits derived from the endophytes in an environment more similar to a field environment. Also of great significance was that this study demonstrated that the improvements were most significant for barley inoculated with a combination of all five endophytes.

In the specification the terms "comprise, comprises, comprised and comprising" or any variation thereof and the terms "include, includes, included and including" or any variation thereof are considered to be totally interchangeable and they should all be afforded the widest possible interpretation and vice versa.

The invention is not limited to the embodiments hereinbefore described but may be varied in both construction and detail.

REFERENCES

Murphy B R, Doohan F M, Hodkinson T R. 2014. Yield increase induced by the fungal root endophyte *Piriformospora indica* in barley grown at low temperature is nutrient limited. *Symbiosis* 62: 29-39.

Murphy B R, Doohan F M, Hodkinson T R. 2014. Persistent fungal root endophytes isolated from a wild barley species suppress seed-borne infections in a barley cultivar. *Biocontrol* 60: 281-292.

Murphy B R, Doohan F M, Hodkinson T R. 2015. Fungal root endophytes of a wild barley species increase yield in a nutrient-stressed barley cultivar. *Symbiosis* 65: 1-7.

TABLE 12

Significant negative (−−) and positive (++) differences in barley traits between endophyte-inoculated and control plants grown in optimal conditions (OC) and under multiple stress (MS); 0 indicates no difference, *indicates p < 0.05, **indicates P < 0.01.

| | | Endophyte difference, less (−−) or greater (++) than control | | | | | | |
|---|---|---|---|---|---|---|---|---|
| Trait | OC/MS | 0401IA76 | 040605(2A) | 040605(2C) | 040901(3) | 040906(4) | Allendos | Overall |
| Germination Index (GI) | OC | 0 | 0 | 0 | ++,* | 0 | 0 | 0 |
| | MS | 0 | ++,** | ++,** | 0 | 0 | 0 | 0 |
| Mean number of dead plants per pot | OC | 0 | 0 | 0 | 0 | 0 | 0 | 0 |
| | MS | ++,** | ++,** | ++,** | ++,** | ++,** | ++,** | ++,** |
| Mean height | OC | 0 | ++,** | ++,** | ++,** | ++,** | ++,** | ++,** |
| | MS | ++,** | ++,** | ++,** | ++,** | ++,* | ++,** | ++,** |
| Mean shoot dry weight | OC | ++,** | 0 | 0 | −−,** | 0 | 0 | 0 |
| | MS | ++,* | ++,** | ++,** | 0 | ++,** | ++,** | ++,* |
| Mean root dry weight | OC | −−,* | −−,* | −−,* | −−,* | 0 | −−,* | −−,* |
| | MS | ++,** | ++,** | ++,** | ++,** | ++,** | ++,** | ++,** |
| Mean number of tillers | OC | ++,* | ++,* | 0 | ++,* | 0 | ++,* | ++,* |
| | MS | ++,* | ++,* | ++,** | 0 | ++,** | ++,** | ++,* |
| Overall difference | OC | ++,* | ++,* | 0 | 0 | 0 | 0 | 0 |
| | MS | ++,* | ++,** | ++,** | ++,* | ++,** | ++,** | ++,** |

Murphy B R, Doohan F M, Hodkinson T R. 2015a. Media manipulations and the culture of beneficial fungal root endophytes. *International Journal of Biology* 7(3): 94-102.

Murphy B R, Nieto L M, Doohan F M, Hodkinson T R. 2015b. Profundae diversitas: Genetic diversity of the culturable fungal root endophytes of wall barley (*Hordeum murinum*). *Mycology*, doi: 10.1080/21501203.2015.1070213.

Murphy B R, Nieto L M, Doohan F M, Hodkinson T R. 2015c. Fungal endophytes enhance agronomically important traits in severely drought-stressed barley. *Journal of Agronomy and Crop Science*, doi:10.1111/jac.12139.

Murphy B R, Nieto L M, Doohan F M, Hodkinson T R. 2015d. The difference between life and death: Fungal endophytes improve survival and increase biomass in multiply-stressed barley. *Global Journal of Science Frontier Research* 15(5): 1-9.

Zadoks J C, Chang T T, Konzak C F (1974) A Decimal Code for the Growth Stages of Cereals. Weed Res. 14:415-421.

---

The invention claimed is:

1. A seed coating composition for use in (a) increasing grain yield and dry shoot weight in a plant, the composition comprising a mixture of a fungal root endophyte isolated from a root of the plant and a carrier medium for application of said composition to a target seed, or for (b) increasing tolerance to the development of seed-borne fungal infections on germinated and ungerminated seeds, the composition comprising a mixture of a fungal root endophyte isolated from a root of a plant sprouted from said seeds and a carrier medium for application of said composition to a target seed, wherein the endophyte is characterised in having a nuclear ribosomal internal transcribed spacer (nrITS) with 100% sequence identity to any one of SEQ ID NOs: 3 to 15, wherein the fungal root endophyte is isolated from a root of the plant *Hordeum murinum*, and wherein the plant and seeds are in low-nutrient conditions, or in drought-stressed conditions, or in multiply-stressed conditions.

2. A seed coating composition according to claim 1, wherein the plant is *Hordeum murinum* subsp. *murinum* L. (Hmm).

3. The seed coating composition according to claim 1, wherein the fungal root endophyte is selected based on having a nuclear ribosomal internal transcribed spacer selected from any one of SEQ ID NOs: 3 to 15, or any combination thereof.

4. The seed coating composition according to claim 1, wherein the fungal root endophyte is selected based on having a nuclear ribosomal internal transcribed spacer selected from any one of SEQ ID NOs: 3 to 15, or any combination thereof, and wherein the composition for increasing tolerance to the development of seed-borne fungal infections on germinated and ungerminated seeds planted in low-nutrient, drought-stressed or multiply-stressed conditions comprises the fungal root endophytes having a nuclear ribosomal internal transcribed spacer as defined by SEQ ID NO: 6 or SEQ ID NO: 11.

5. The seed coating composition according to claim 1, wherein the fungal root endophyte is selected based on having a nuclear ribosomal internal transcribed spacer selected from any one of SEQ ID NOs: 3 to 15, or any combination thereof, and wherein the composition for increasing grain yield and dry shoot weight in a plant found in low-nutrient, drought-stressed or multiply-stressed conditions comprises at least one of the fungal endophyte isolates having a nuclear ribosomal internal transcribed spacer as defined by SEQ ID NO: 6, SEQ ID NO: 7 or SEQ ID NO: 8.

6. The seed coating composition according to claim 1, wherein the fungal root endophyte is selected based on having a nuclear ribosomal internal transcribed spacer selected from any one of SEQ ID NOs: 3 to 15, or any combination thereof, and wherein the composition for increasing tolerance to the development of seed-borne fungal infections on germinated and ungerminated seeds planted in low-nutrient, drought-stressed or multiply-stressed conditions comprises the fungal root endophytes having a nuclear ribosomal internal transcribed spacer as defined by SEQ ID NO: 6, SEQ ID NO: 8, SEQ ID NO: 13, SEQ ID NO: 14 or SEQ ID NO: 15.

7. The seed coating composition according to claim 1, wherein the fungal root endophyte is selected based on having a nuclear ribosomal internal transcribed spacer selected from any one of SEQ ID NOs: 3 to 15, or any combination thereof, and wherein the composition for increasing grain yield and dry shoot weight in a plant found in low-nutrient, drought-stressed or multiply-stressed conditions comprises at least one of the fungal endophyte isolates having a nuclear ribosomal internal transcribed spacer as defined by SEQ ID NO: 6, SEQ ID NO: 8, SEQ ID NO: 13, SEQ ID NO: 14 OR SEQ ID NO: 15.

8. The seed coating composition according to claim 1, wherein the concentration of the fungal endophyte isolate in the composition is between 0.001% (w/v) to 1.0% (w/v).

9. The seed coating composition according to claim 1, wherein the carrier medium is selected from water, distilled water, sterilised water, sterilised distilled water, an emulsified suspension, wettable powder, encapsulation of spores of the fungal endophyte in alginate beads, or a film-coating.

10. A seed coated with, mixed with or encapsulated with the composition of any one of claim 1.

11. A seed mixed with the composition according to claim 1, in which the carrier medium is alginate beads.

12. A method of preparing a seed having (a) increased grain yield and dry shoot weight or (b) with increased tolerance to the development of seed-borne fungal infections on germinated and ungerminated seeds, the method comprising the step of inoculating the seed with a fungal root endophyte isolated from a root of a plant which produced said seed, wherein the endophyte is characterised in having a nuclear ribosomal internal transcribed spacer (nrITS) with 100% sequence identity to any one of SEQ ID NOs: 3 to 15, wherein the fungal root endophyte is isolated from a root of the plant *Hordeum murinum*, and wherein the plant and seeds are in low-nutrient conditions, or in drought-stressed conditions, or in multiply-stressed conditions.

13. The method according to claim 12, wherein the plant is *Hordeum murinum* subsp. *murinum* L. (Hmm).

14. The method according to claim 12, wherein the fungal root endophyte is selected based on having a nuclear ribosomal internal transcribed spacer selected from any one of SEQ ID NOs: 3 to 15, or any combination thereof.

15. The method according to claim 12, wherein the fungal root endophyte is selected based on having a nuclear ribosomal internal transcribed spacer selected from any one of SEQ ID NOs: 3 to 15, or any combination thereof, and wherein the method for preparing a seed with increased tolerance to the development of seed-borne fungal infections on germinated and ungerminated seeds comprises inoculating the seed with a fungal root endophyte having a nuclear ribosomal internal transcribed spacer as defined by SEQ ID NO: 6 or SEQ ID NO: 11, or variants thereof.

16. The method according to claim 12, wherein the fungal root endophyte is selected based on having a nuclear ribosomal internal transcribed spacer selected from any one of SEQ ID NOs: 3 to 15, or any combination thereof, and wherein the method for increasing grain yield and dry shoot weight in a plant comprises inoculating the seed with at least one of the fungal endophyte isolates having a nuclear ribosomal internal transcribed spacer as defined by SEQ ID NO: 6, SEQ ID NO: 7 or SEQ ID NO: 8.

17. The method according to claim 12, wherein the fungal root endophyte is selected based on having a nuclear ribosomal internal transcribed spacer selected from any one of SEQ ID NOs: 3 to 15, or any combination thereof, and wherein the method for preparing a seed with increased tolerance to the development of seed-borne fungal infections on germinated and ungerminated seeds comprises inoculating the seed with a fungal root endophyte having a nuclear ribosomal internal transcribed spacer as defined by SEQ ID NO: 6, SEQ ID NO: 8, SEQ ID NO: 13, SEQ ID NO: 14 or SEQ ID NO: 15.

18. A method according to claim 12, wherein the fungal root endophyte is selected based on having a nuclear ribosomal internal transcribed spacer selected from any one of SEQ ID NOs: 3 to 15, or any combination thereof, and wherein the method for increasing grain yield and dry shoot weight in a plant comprises inoculating the seed with at least one of the fungal endophyte isolates having a nuclear ribosomal internal transcribed spacer as defined by SEQ ID NO: 6, SEQ ID NO: 8, SEQ ID NO: 13, SEQ ID NO: 14 OR SEQ ID NO: 15.

19. The method according to claim 12, wherein the concentration of the fungal endophyte isolate is between 0.001% (w/v) to 1.0% (w/v).

20. The method according to claim 12, wherein the carrier medium is selected from water, distilled water, sterilised water, sterilised distilled water, an emulsified suspension, wettable powder, encapsulation of spores of the fungal endophyte in alginate beads, or a film-coating.

* * * * *